US009119869B2

(12) United States Patent
Shebuski et al.

(10) Patent No.: US 9,119,869 B2
(45) Date of Patent: Sep. 1, 2015

(54) MUCIN DERIVED POLYPEPTIDES

(76) Inventors: Ronald J. Shebuski, Alexandria, VA (US); Samuel B. Ho, San Diego, CA (US); Laurie Shekels, Orono, MN (US); Robert L. Heinrikson, Plainwell, MI (US)

( * ) Notice: Subject to any disclaimer, the term of this patent is extended or adjusted under 35 U.S.C. 154(b) by 259 days.

(21) Appl. No.: 13/097,680

(22) Filed: Apr. 29, 2011

(65) Prior Publication Data

US 2012/0028911 A1 Feb. 2, 2012

Related U.S. Application Data

(60) Provisional application No. 61/329,193, filed on Apr. 29, 2010.

(51) Int. Cl.
| | | |
|---|---|---|
| A61K 38/00 | (2006.01) | |
| A61K 45/06 | (2006.01) | |
| A61K 31/7088 | (2006.01) | |
| A61K 38/17 | (2006.01) | |
| A61P 1/00 | (2006.01) | |
| A61P 29/00 | (2006.01) | |
| C07K 19/00 | (2006.01) | |
| A61K 39/00 | (2006.01) | |
| C07K 14/47 | (2006.01) | |

(52) U.S. Cl.
CPC .......... *A61K 31/7088* (2013.01); *A61K 38/1735* (2013.01); *A61K 39/0008* (2013.01); *A61K 45/06* (2013.01); *C07K 14/4727* (2013.01); *A61K 38/00* (2013.01); *C07K 2319/00* (2013.01); *C07K 2319/036* (2013.01); *C07K 2319/21* (2013.01); *C07K 2319/22* (2013.01); *C07K 2319/23* (2013.01); *C07K 2319/41* (2013.01); *C07K 2319/43* (2013.01); *C07K 2319/60* (2013.01); *C07K 2319/61* (2013.01)

(58) Field of Classification Search
CPC ........... A61K 2300/00; A61K 38/1735; A61K 38/00; A61K 45/06; C07K 14/4727; C07K 2319/00; C07K 2319/036; C07K 2319/21; C07K 2319/22; C07K 2319/23; C07K 2319/41; C07K 2319/43
USPC .......................................... 514/20.9; 530/395
See application file for complete search history.

(56) References Cited

U.S. PATENT DOCUMENTS

| 6,063,755 | A | 5/2000 | Podolsky | |
|---|---|---|---|---|
| 6,221,840 | B1 | 4/2001 | Podolsky | |
| 6,235,709 | B1 | 5/2001 | Kodama et al. | |
| 7,078,188 | B2 | 7/2006 | Batra et al. | |
| 2008/0153104 | A1* | 6/2008 | Aburatani et al. | 435/7.1 |
| 2009/0131310 | A1 | 5/2009 | Ho et al. | |
| 2010/0240872 | A1* | 9/2010 | Nakano | 530/387.3 |
| 2012/0021987 | A1 | 1/2012 | Ho et al. | |
| 2012/0028911 | A1 | 2/2012 | Shebuski et al. | |

FOREIGN PATENT DOCUMENTS

| WO | 01/04152 | 1/2001 |
|---|---|---|
| WO | 02/11673 | 2/2002 |
| WO | 02/22660 | 3/2002 |
| WO | 2005/111070 | 7/2006 |

OTHER PUBLICATIONS

SEQ ID No. 85 from US 2008/0153104, published Jun. 2008.*
Nicolaou KC, Chen JS, Edmonds DJ, Estrada AA, "Recent Advances in the Chemistry and Biology of Naturally Occurring Antibiotics," Angew Chem Int Ed Engl. 2009, 48(4): 660-719.*
Crawley, Suzanne C., et al., Genomic Organization and Structure of the 3' Region of Human MUC3: Alternative Splicing Predicts Membrane-Bound and Soluble Forms of the Mucin, Biochemical and Biophysical Research Communications 263 (3), 728-736 (Oct. 5, 1999), Academic Press.
Gum, James R., Jr., et al., Initiation of Transcription of the MUC3A Human Intestinal Mucin from a TAT-less Promoter and Comparison with the MUC3B Amino Terminus, the Journal of Biological Chemistry, vol. 278, No. 49, Issue of Dec. 5, pp. 49600-49609, 2003, Epub Sep. 4, 2003.
Gum, James R., Jr., et al., MUC3 Human Intestinal Mucin, The Journal of Biological Chemistry, vol. 272, No. 42, Issue of Oct. 17, 1997, pp. 26678-26688.
Gum, James R., Jr., et al., MUC17, a Novel Membrane-Tethered Mucin, Biochemical and Biophysical Research Communications, 291(3), 466-475 (Mar. 1, 2002).
Ho, Jennie J.L., et al., N-glycosylation is required for the surface localization of MUC17 mucin, International Journal of Oncology 23(3): 585-592, Sep. 2003.
Ho, Samuel B., et al., EGF-like Domains of the MUC3 intestinal Membrane-Bound Mucin Promote Cell Migration and Accelerate Intestinal Wound Healing, Gastroenterology 126 (No. 4) Suppl 2: A65-66, 510, (2004).
Kyo, Kennoki, et al., Associations of distinct variants of the intestinal mucin gene MUC3A with Ulcerative colitis and Crohn's disease, J Hum Genet (2001) 46(1):5-20, Jpn Soc Genet and Springer-Verlag (2001).
Leroy, Xavier, Quantitative RT-PCR Assay for MUC3 and VEGF mRNA in Renal Clear Cell Carcinoma: Relationships with Nuclear Grade and Prognosis, Urology 62 (4), Oct. 2003, 771-775, Elsevier, Inc.
Pratt, Wendy S., et al., Multiple Transcripts of MUC3: Evidence for Two Genes, MUC3A and MUC3B, Biochemical and Biophysical Research Communications 275(3), 916-923 (Sep. 2000), Academic Press.

(Continued)

*Primary Examiner* — Julie Ha
(74) *Attorney, Agent, or Firm* — Honigman Miller Schwartz and Cohn LLP; Kelly T. Murphy; Jonathan P. O'Brien

(57) ABSTRACT

Isolated MUC17, Muc3 or MUC3 derived polypeptides and polynucleotides encoding the same are described. The MUC17, Muc3 or MUC3 derived polypeptides, polynucleotides, and pharmaceutical compositions can be used to treat gastrointestinal tract diseases and disorders including, inflammatory bowel disease and its associated colitides, for example, Crohn's Disease.

9 Claims, 11 Drawing Sheets

(56) References Cited

OTHER PUBLICATIONS

Shekels, Laurie L., et al., Closing and characterization of mouse intestinal MUC3 mucin: 3' sequence contains epidermal-growth-factor-like domains, Biochem. J (Mar. 15, 1998) 330 (pt 3), 1301-1308.

Shekels, Laurie L., et al., Comparison of Murine Membrane-bound Muc3 and Muc4 Promotor Sequences and Expression of Muc2, Muc3 and Muc4 Mucins During Experimental Colitis, Gastroenterology 120:A193-4, 1018, 2001.

Shekels, Laurie L., et al., Biological Activity of the Human Muc 17 Membrane-bound Mucin Cysteine-Rich Domain is Mediated by ERK and PI-3 Kinase Pathways, Gastroenterology, 132 (No. 4) Suppl 2, A569, T1850, 2007.

Shekels, Laurie L., et al., Characterization of the mouse MUC3 membrane bound intestinal mucin 5' coding and promoter regions: regulation by inflammatory cytokines, Biochimica et Biophysics Acta 1627 (2003) 90-100, Elsevier Science B.V.

Shekels, Laurie L., et al., Mouse gastric mucin: cloning and chromosomal localization, Biochem J. (1995) 311, 7.

Strausberg, Robert L., et al., Generation and initial analysis of more than 15,000 full-length human and mouse cDNA sequences, Proc Natl Acad Sci USA, Dec. 24, 2002, vol. 99 No. 26, 16899-16903, Epub Dec. 11, 2002.

Van Klinken, B. Jan-Wilem, et al., Molecular Cloning of Human MUC3 cDNA Reveals a Novel 59 Amino Acid Tandem Repeat Region, Biochemical and Biophysical Research Communications, 238(1), 143-148 (Sep. 8, 1997), Academic Press.

Williams, Stephanie J., et al., The MUC3 Gene Encodes a Transmembrance Mucin and is Alternatively Spliced, Biochemical and Biophysical Research Communications 261 (1), 83-89 (Jul. 22, 1999), Academic Press.

ISR from PCT/US2005/016794 Dated May 31, 2006.

Supplemental Search Report from the EP 05778962 Dated Sep. 4, 2007.

* cited by examiner

FIG. 1

SEQ ID NO. 1: (MUC17 CRD1-L-CRD2 polypeptide)

RTTTCFGDGCQNTASRCKNGGTWDGLKCQCPNLYYGELCEEVVSSIDIGPPETISAQME
LTVTVTSVKFTEELKNHSSQEFQEFKQTFTEQMNIVYSGIPEYVGVNITKLRLGSVVVEH
DVLLRTKYTPEYKTVLDNATEVVKEKITKVTTQQIMINDICSDMMCFNTTGTQVQNITV
TQYDPEEDCRKMAKEYGDYFVVEYRDQKPYCISPCEPGFSVSKNCNLGKCQMSLSGPQ
CLCVTTETHWYSGETCNQGTQK

SEQ ID NO. 2: (MUC17 CRD1-L-CRD2 polypeptide) (Serine C-terminal A.A.)

RTTTCFGDGCQNTASRCKNGGTWDGLKCQCPNLYYGELCEEVVSSIDIGPPETISAQME
LTVTVTSVKFTEELKNHSSQEFQEFKQTFTEQMNIVYSGIPEYVGVNITKLRLGSVVVEH
DVLLRTKYTPEYKTVLDNATEVVKEKITKVTTQQIMINDICSDMMCFNTTGTQVQNITV
TQYDPEEDCRKMAKEYGDYFVVEYRDQKPYCISPCEPGFSVSKNCNLGKCQMSLSGPQ
CLCVTTETHWYSGETCNQGTQKS

SEQ ID NO: 3: (MUC17 CRD1-L polypeptide)

RTTTCFGDGCQNTASRCKNGGTWDGLKCQCPNLYYGELCEEVVSSIDIGPPETISAQME
LTVTVTSVKFTEELKNHSSQEFQEFKQTFTEQMNIVYSGIPEYVGVNITKLRLGSVVVEH
DVLLRTKYTPEYKTVLDNATEVVKEKITKVTTQQIMINDICSDMMCFNTTGTQVQNITV
TQYDPEEDCRKMAKEYGDYFVVEYRDQKP

SEQ ID NO:4: (MUC17 L-CRD2 polypeptide)

TISAQMELTVTVTSVKFTEELKNHSSQEFQEFKQTFTEQMNIVYSGIPEYVGVNITKLRLG
SVVVEHDVLLRTKYTPEYKTVLDNATEVVKEKITKVTTQQIMINDICSDMMCFNTTGTQ
VQNITVTQYDPEEDCRKMAKEYGDYFVVEYRDQKPYCISPCEPGFSVSKNCNLGKCQM
SLSGPQCLCVTTETHWYSGETCNQGTQK

SEQ ID NO:5: (MUC17 L-CRD2 polypeptide) (Serine C-terminal A.A.)

TISAQMELTVTVTSVKFTEELKNHSSQEFQEFKQTFTEQMNIVYSGIPEYVGVNITKLRLG
SVVVEHDVLLRTKYTPEYKTVLDNATEVVKEKITKVTTQQIMINDICSDMMCFNTTGTQ
VQNITVTQYDPEEDCRKMAKEYGDYFVVEYRDQKPYCISPCEPGFSVSKNCNLGKCQM
SLSGPQCLCVTTETHWYSGETCNQGTQKS

FIG. 5A (1) Mouse Muc3 CRD1-L-CRD2-His[8] (I-1 through G-286).

cmnggiwtgdkcICPNGFGGDRCENIVNVVNCENGGTWDGLKCQCTSL
FYGPRCEELVESVEIEPTVAASVEVSVTVTSQEYSEKLQDRKSEEFS
NFNKTFTKQMALIYAGIPEYEGVIIKNLSKGSIVVDYDVILKAKYTPGF
ENTLDTVVKNLETKIKNATEVQVQDVNNNCSALLCFNSTATKVQNSA
TVSVNPEETCKKEAGEDFAKFVTLGQKGDKWFCITPCSAGYSTSKN
CSYGKCQLQRSGPQCLCLITDTHWYSGENCDWGIQKSLVYG-
HHHHHHHH (2) Mouse Muc-3 CRD1-(11 amino acid spacer)-Lcys domain- CRD2.

cmnggiwtgdkcICPNGFGGDRCENIVNVVNCENGGTWDGLKCQCTSL
FYGPRCEELVE(PGSGSDGSDGS)NNNCSALLCFNSTATKVQNSATV
SVNPEETCKKEAGEDFAKFVTLGQKGDKWFCITPCSAGYSTSKNCS
YGKCQLQRSGPQCLCLITDTHWYSGENCDWGIQKslvygHHHHHHHH (3) Mouse Muc-3 CRD1-(20 amino acid spacer)-Lcys-CRD2 cmnggiwtgdkcICPNGFGGDRCENIVNVVNCENGGTWDGLKCQCTSL
FYGPRCEELVE(FLKPQHPGSGSDGSDGSAQI)NNNCSALLCFNSTA
TKVQNSATVSVNPEETCKKEAGEDFAKFVTLGQKGDKWFCITPCSA
GYSTSKNCSYGKCQLQRSGPQCLCLITDTHWYSGENCDWGIQKslvy
gHHHHHHHH (4) Linker Domain-SEA module Muc 3.

SVEIEPTVAASVEVSVTVTSQEYSEKLQDRKSEEFSNFNKTFTKQMA
LIYAGIPEYEGVIIKNLSKGSIVVDYDVILKAKYTPGFENTLDTVVKNLE
TKIKNATEVQVQDV

FIG. 5B (5) Human GST-MUC17CRD1-Linker-CRD2 (R-1 through S-260).

(Glutathione-S-Transferase)-RTTTCFGDGCQNTASRCKNGGTW
DGLKCQCPNLYYGELCEEVVSSIDIGPP<u>ETISAQMELT</u>
<u>VTVTSVKFTEELKNHSSQEFQEFKQTFTEQMNIVYSGI</u>
<u>PEYVGVNITKLRLGSVVV</u>EHDVLLRTKYTPEYKTVLDN
ATEVVKEKITKVTTQQIMINDICSDMMCFNTTGTQVQNI
TVTQYDPEEDCRKMAKEYGDYFVVEYRDQKPYCISPC
EPGFSVSKNCNLGKCQMSLSGPQCLCVTTETHWYSGE
TCNQGTQKS (6) Human MUC17CRD1-L-CRD2-His⁸ (R-1 through K-259).

MRTTTCFGDGCQNTASRCKNGGTWDGLKCQCPNLYY
GELCEEVVSSIDIGPP<u>ETISAQMELTVTVTSVKFTEELK</u>
<u>NHSSQEFQEFKQTFTEQMNIVYSGIPEYVGVNITKLRL</u>
<u>GSVVV</u>EHDVLLRTKYTPEYKTVLDNATEVVKEKITKVT
TQQIMINDICSDMMCFNTTGTQVQNITVTQYDPEEDCR
KMAKEYGDYFVVEYRDQKPYCISPCEPGFSVSKNCNL
GKCQMSLSGPQCLCVTTETHWYSGETCNQGTQKslvyg
HHHHHHHH (7) Full-length sequence of MUC17 CRD1-L-CRD2 as expressed in baculovirus-insect cell system.

[AMVHHHHHHSAGLVPRGSGKETAAAKFERQHMDSAS
GGGDDDKSPGFSSKGLDPNSSSKLSMG]RTTTCFGD
GCQNTASRCKNGGTWDGLKCQCPNLYYGELCEEVVS
SIDIGPP<u>ETISAQMELTVTVTSVKFTEELKNHSSQEFQE</u>
<u>FKQTFTEQMNIVYSGIPEYVGVNITKLRLGSVVV</u>EHDV
LLRTKYTPEYKTVLDNATEVVKEKITKVTTQQIMINDIC
SDMMCFNTTGTQVQNITVTQYDPEEDCRKMAKEYGDY
FVVEYRDQKPYCISPCEPGFSVSKNCNLGKCQMSLSG
PQCLCVTTETHWYSGETCNQGTQKslvyg HHHHHHHH

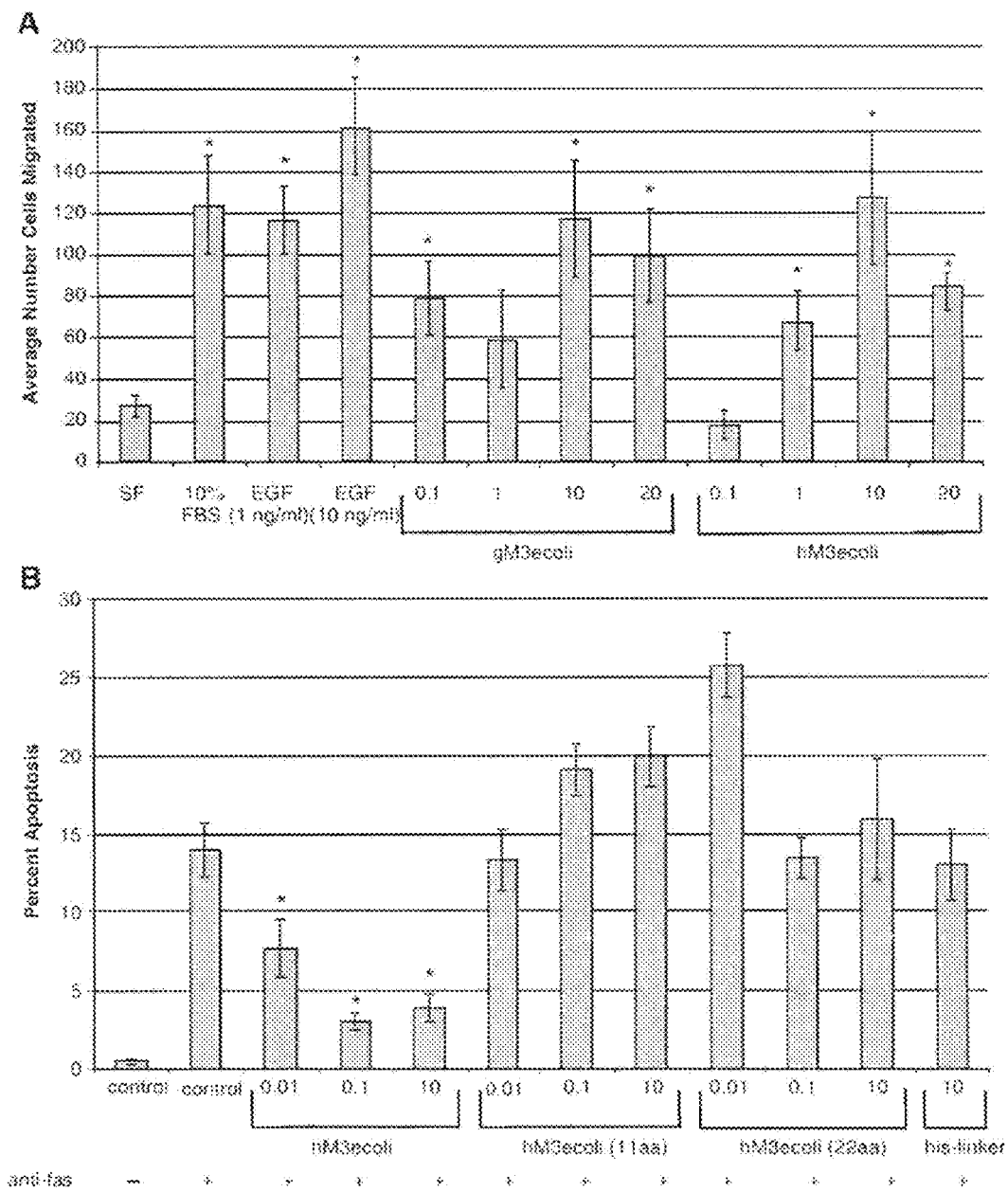

FIG. 7
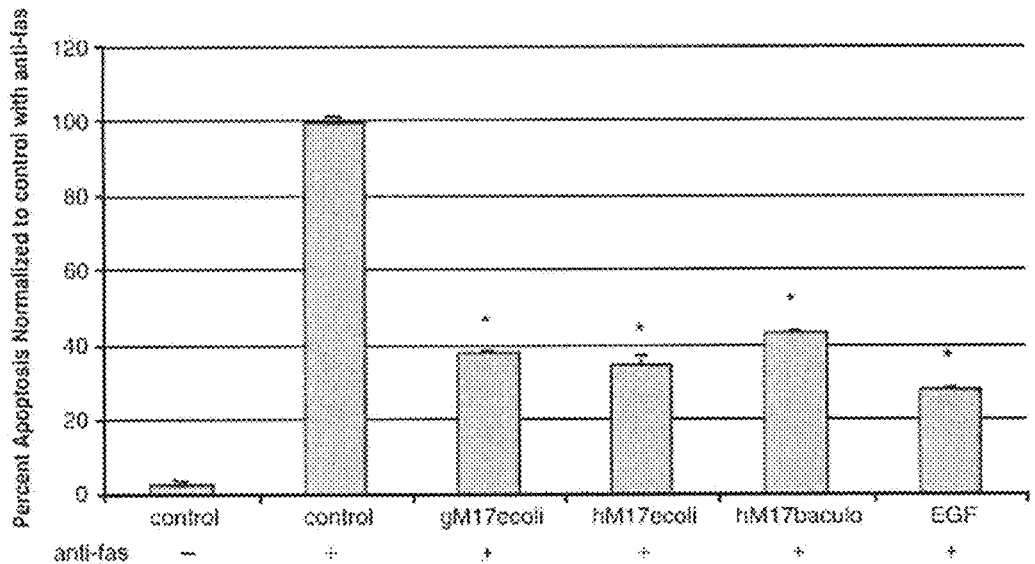
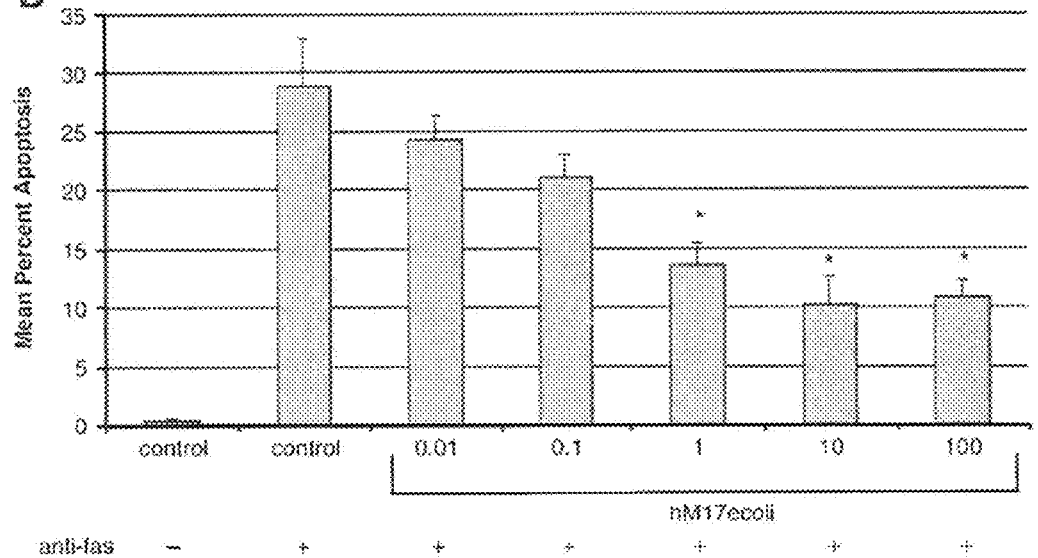
* = p < 0.01 vs. no treatment

* SF vs. FBS p < 0.05, N = 6 samples each

MUCIN DERIVED POLYPEPTIDES

PRIORITY

This application claims priority to U.S. Provisional Application No. 61/329,193, filed Apr. 29, 2010, the contents of which are incorporated by reference in their entirety.

GOVERNMENT SUPPORT

This invention was made with government support under a Veterans Administration (VA) Merit Review Grant (SBH), National Institutes of Health (NIH) STTR grant G1 R43DK072629-01, NIH center grant (DK080506), and the Research Service of the Department of Veterans Affairs. The U.S. government may have certain rights in the invention.

SEQUENCE LISTING

This application incorporates by reference in its entirety the Sequence Listing entitled "Mucin_ST25.txt" (28.0 KB), which was created on Apr. 27, 2011 and filed electronically herewith.

FIELD

The present disclosure relates to therapeutic mucin proteins. In particular, the present technology relates to isolated MUC17, Muc3 or MUC3 derived polypeptides and polynucleotides encoding the same that can be used to treat gastrointestinal diseases and disorders, for example, Inflammatory Bowel Disease (IBD), which encompasses ulcerative colitis, Crohn's disease and other colitides.

BACKGROUND

The statements in this section merely provide background information related to the present disclosure and may not constitute prior art.

Mucins are a family of secreted and cell-surface glycoproteins expressed by most epithelial tissues. Mucins are directed to the surface of epithelial tissues and are thought to play a protective role. Alterations in mucin proteins have been noted in conditions such as gastritis and peptic ulcer disease, Crohn's disease, ulcerative colitis, and intestinal cancers. Mucins can be grouped into two categories, secreted mucin proteins or membrane-bound mucin proteins. Secreted mucins are characterized by carboxyl- and amino-terminal domains termed "Von Willebrand-type D" domains that flank a large serine and threonine-rich domain that is heavily glycosylated. These mucins are able to join end-to-end to form long polymers that are highly viscous in solution. Membrane-bound mucins are characterized by a carboxyl-terminal domain containing a small cytoplasmic domain, a hydrophobic membrane-spanning domain, and an extracellular domain that is characterized in some cases by a cysteine-rich domain and a large serine- and threonine-rich glycosylated domain. Messenger RNA splice variants of these genes have been described that encode proteins without the membrane-spanning domain, which allows them to function as a secreted monomeric mucin. In this regard the membrane-spanning mucins can be considered bi-functional, existing as both membrane-associated proteins and as secreted proteins.

The etiology of IBD is not well understood. However, pre-clinical data in rodent models of IBD indicate that treatment with *E. coli*-derived mucins (Mouse Muc3 proteins) prevents and reverses the ulcerations of the colonic wall and decreases the accompanying chronic symptoms of diarrhea and body weight loss.

IBD is prevalent in the United States and Western Europe and currently estimated to afflict 1.2 million people in the United States with approximately 30,000 new cases diagnosed each year. Worldwide, it is estimated that 4 million people suffer from IBD. In addition, IBD has been associated with an increased risk of colorectal cancer. To date there are no approved medications to treat IBD that act by restoring the epithelial layer of the intestine or colon. Currently there is no known cure for IBD and existing drug therapies are only utilized to suppress symptoms. In addition, current therapies are associated with significant toxicities.

Ulcerative colitis is a common form of IBD. Ulcerative colitis is generally recognized as an immune-mediated disorder resulting from an abnormal interaction between colonic microflora and mucosal immune cells in a genetically susceptible host. The nature of the mucosal immune abnormality remains unclear, and how this interaction develops is not well understood. In addition, all drugs currently on the market for the treatment of ulcerative colitis have side effects and none of them can cure the disease. Oral mucositis is a condition that occurs in cancer patients treated for head and neck cancer with chemotherapy or radiation and has no accepted therapy The current treatments for IBD are often only partially effective and have numerous toxicities. Thus, there is a need for additional treatment compositions and modalities to treat IBD and related colitides that are safe and do not induce cellular proliferation or increase the risk of tumorgenesis.

SUMMARY

In one aspect, the present technology provides polypeptides derived from MUC17, Muc3 and MUC3 mucin proteins and polynucleotides that encode them. Isolated MUC17, Muc3 or MUC3 derived polypeptides include: MUC17, Muc3 or MUC3 CRD1-L-CRD2, CRD1-L and L-CRD2 polypeptides. Exemplary MUC17, Muc3 or MUC3 CRD1-L-CRD2, CRD1-L and L-CRD2 polypeptides include amino acid sequences that are provided in SEQ ID NO: 1-5. The isolated MUC17, Muc3 or MUC3 CRD1-L-CRD2, CRD1-L and L-CRD2 polypeptides have been shown to be capable of inducing cell migration and demonstrate low potential for cellular proliferation.

In another aspect, the present technology provides pharmaceutical compositions comprising MUC17, Muc3 or MUC3 derived polypeptides wherein at least one polypeptide from MUC17, Muc3 or MUC3 CRD1-L-CRD2, CRD1-L and L-CRD2 is added to at least one pharmaceutically acceptable excipient. Pharmaceutical compositions of the present technology can be administered orally, rectally, parentally, including, intravenously, mucosally, subcutaneously, intranasally, via inhalation (e.g., aerosol inhalation), locally, infusion, via a catheter, via a lavage, or by any other method or any combination of the foregoing as would be practiced by one of ordinary skill in the art.

In a further aspect, the present technology provides for a method for treating a subject having IBD or other related colitides disease or disorder, the method including, administering to the subject a therapeutically effective dose of at least one MUC17, Muc3 or MUC3 derived polypeptide comprising MUC17, Muc3 or MUC3 CRD1-L-CRD2, CRD1-L or L-CRD2 polypeptides or polynucleotides encoding the same or a pharmaceutically acceptable salt thereof. In some aspects, the pharmaceutical dose of the at least one MUC17, Muc3 or MUC3 derived polypeptide comprising MUC17, Muc3, or MUC3 CRD1-L-CRD2, CRD1-L, L-CRD2 or combinations thereof is formulated with at least one pharmaceutically acceptable carrier, diluent or excipient suitable for a recommended route of administration commonly practiced by those of ordinary skill in the art.

Unless otherwise defined, all technical and scientific terms used herein have the same meaning as commonly understood by one of ordinary skill in the art to which this present technology belongs. Although methods and materials similar or equivalent to those described herein can be used in the practice or testing of the present technology, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the present technology are set forth in the accompanying figures and the description below. Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 depicts amino acid sequences of MUC17-derived CRD1-L-CRD2, CRD1-L and L-CRD2 polypeptides, in accordance with several embodiments of the present technology.

FIGS. 4A-4D depict a schematic representation of the human MUC17 protein and amino-acid sequences of human MUC17 domains/units. FIG. 4A depicts the general schema of the CRD1-L-CRD2 polypeptide within the 259-residue Cys-rich region, which includes the domains: CRD1, the Linker-SEA (L) domain, L-Cys segment and CRD2. These sequences correspond to the CRD1-L-CRD1 polypeptide of the present technology. FIG. 4B is a comparative sequence overlay of the Cys-rich regions of CRD1 and CRD2 polypeptides of human MUC17 and MUC3, and mouse Muc3 with themselves and with human Epidermal Growth Factor (EGF). FIG. 4C is a comparative sequence overlay of the segment of amino acids preceding CRD2, herein defined as L-Cys. FIG. 4D is a comparative sequence overlay within the segment of amino acids preceding CRD1 of human MUC17, MUC3 and mouse Muc3.

FIGS. 5A-B depict amino acid sequences of mucin-derived proteins in accordance with several embodiments described below.

FIG. 6A is a graph depicting the ability of GST-tagged mouse Muc3 polypeptide CRD1-L-CRD2 and of poly-His tagged mouse Muc3 construct of CRD1-L-CRD2 (both expressed in E. coli) to induce cell migration of LoVo cells in vitro when compared to EGF controls and 10% Fetal Bovine Serum and serum free conditions. Numbers indicate concentration in µg/ml.

FIG. 6B is a graph depicting the ability of poly-His tagged mouse Muc3 polypeptide CRD1-L-CRD2 and Linker-SEA region truncated constructs of mouse Muc3 construct of CRD1-L-CRD2 (hM3ecoli (11aa spacer)+L-Cys; hM3ecoli (20aa spacer)+L-Cys; His-Linker-SEA (L) region alone minus L-Cys) to inhibit apoptosis in the presence of anti-fas in LoVo cells. Numbers indicate concentration in µg/ml; C=control (no protein).

FIG. 7A is a graph depicting the ability of GST-tagged and poly-His tagged human MUC17 polypeptide CRD1-L-CRD2 expressed in E. coli and baculovirus to inhibit apoptosis in LoVo cells in the presence of anti-fas. Data are represented as normalized to maximum apoptosis observed with control with anti-fas from experiments performed at different times FIG. 7B is a graph depicting the ability of varying doses of poly-His tagged human MUC17 polypeptide CRD1-L-CRD2 expressed in E. coli to inhibit apoptosis in LoVo cells in the presence of anti-fas.

Figure 8:
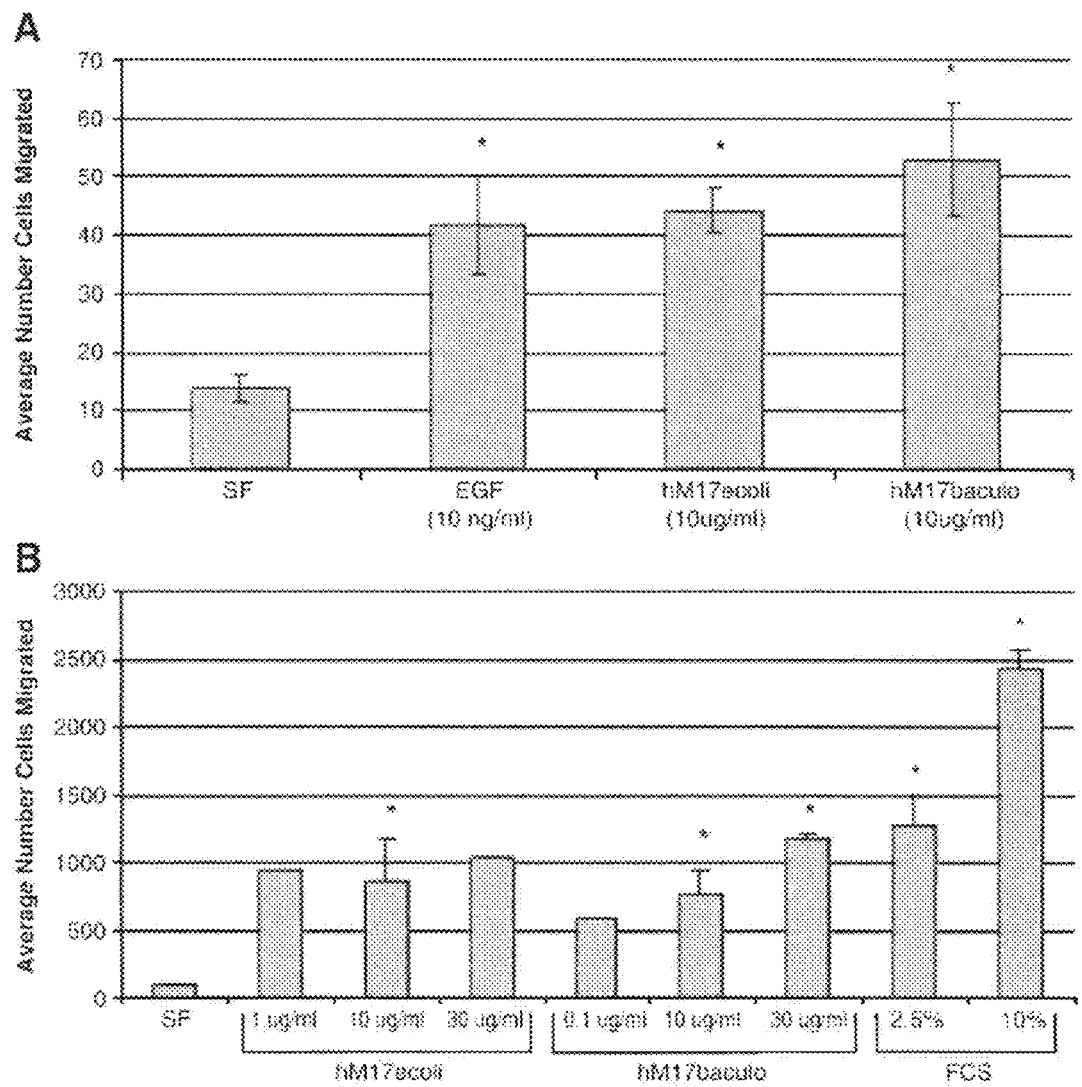

FIG. 8A is a graph depicting the ability of poly-His tagged human MUC17 polypeptide CRD1-L-CRD2 expressed in E. coli and baculovirus to induce LoVo cells to migrate across a razor scrape when compared to an EGF positive control.

FIG. 8B is a graph depicting the ability of varying doses of poly-His tagged human MUC17 polypeptide CRD1-L-CRD2 expressed in E. coli and baculovirus to induce IEC6 cells to migrate across a razor scrape when compared to fetal calf serum.

Figure 9:
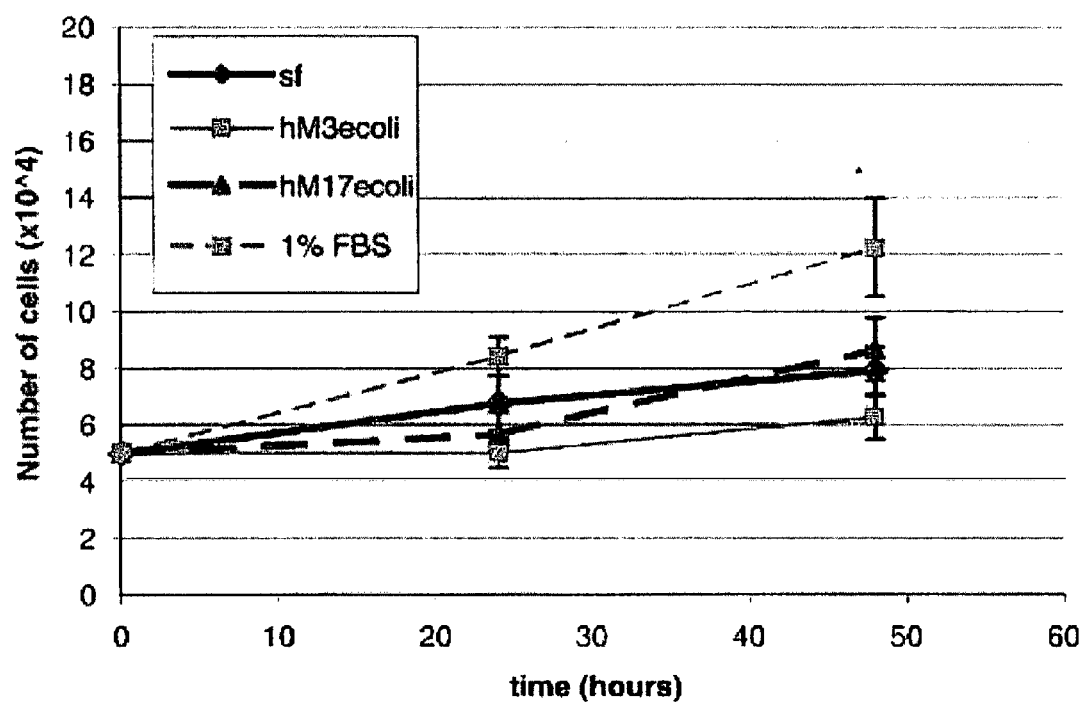

FIG. 9 is a line graph representing the cellular proliferation of LoVo cells in the presence of poly-His-tagged human MUC3 and human MUC17 CRD1-L-CRD2 polypeptides expressed in E. coli when compared to serum-free and fetal bovine serum controls over a period of time.

Figure 10:
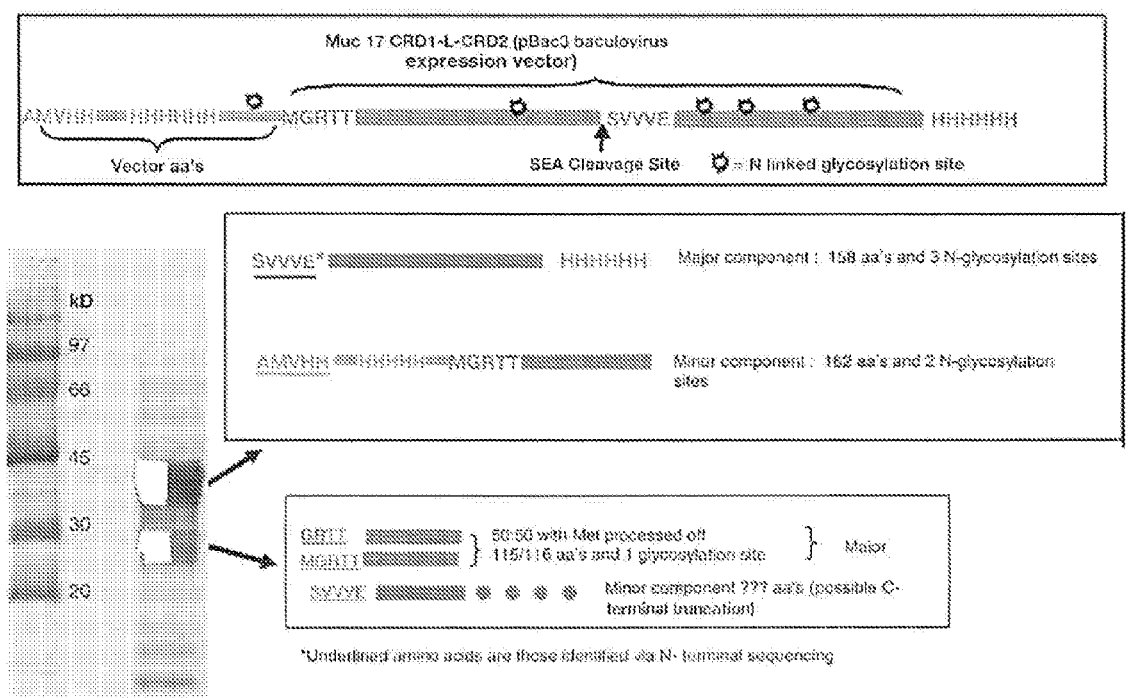

FIG. 10 depicts an N-terminal sequence analysis of baculovirus-insect cell-derived MUC17 CRD1-L-CRD2. Automated Edman degradation was performed with the aid of an Applied Biosystems Model 494 Protein Sequencer fitted with an HPLC for analysis of PTH amino acids. Protein samples were cut from PVDF-blots of the SDS-PAGE gels as indicated and subjected to N-terminal amino acid sequence analysis. There were 2 major bands accounting for >95% of the proteins present. Half of each stained band was cut out and separately subjected to Edman degradation. The upper band consists of a major component beginning at the SEA cleavage site with 3 glycosylation sites and a minor component beginning at the vector His tag. The lower band is a mixture of proteins with the N-terminal with or without the amino acid Met and a minor component with the N-terminal end at the SEA cleavage site (see amino acid data in Table 1).

DETAILED DESCRIPTION

The following description of technology is merely exemplary in nature of the subject matter, manufacture and use of one or more present inventions, and is not intended to limit the scope, application, or uses of any specific present technology claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the present disclosure is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

Unless otherwise defined, all technical and scientific terms used herein have the same meaning as commonly understood by one of ordinary skill in the art to which this present technology belongs. Although methods and materials similar or equivalent to those described herein can be used in the practice or testing of the present technology, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The present technology provides isolated MUC17, Muc3 or MUC3 derived polypeptides and nucleic acids encoding such polypeptides that include a linker domain (L) and one or more Epidermal Growth Factor (EGF)-like cysteine rich domains (CRD) derived from MUC17, Muc3 or MUC3 mucin proteins. As used herein, the term "MUC17, Muc3 or MUC3 derived polypeptides" refers to isolated or purified proteins and polypeptides, including fusion and tagged proteins, which contain amino acid sequences that are derived from MUC17, Muc3 or MUC3 mucin proteins and include at least one CRD and a Linker domain. The linker domain (L) contains an SEA (sea urchin sperm protein, enterokinase, and agrin) module and Linker residues before and after the module. SEA domains are found in several membrane-associated mucins and other membrane proteins and are thought to be important in the non-covalent association of protein subunits, and may play a role in the release of membrane protein subunits at the cell surface. The MUC17, Muc3 or MUC3 derived polypeptides include CRD1-L-CRD2, CRD1-L and L-CRD2 from MUC17, Muc3 or MUC3 mucin proteins and combinations thereof. In an exemplary embodiment, the amino acid sequences of the human MUC17 derived polypeptides of the present technology are provided in SEQ ID NOS: 1-5 as shown in FIG. 1.

In another aspect, the present technology also provides pharmaceutical compositions comprising these polypeptides and/or nucleic acids encoding the same and methods for treating gastrointestinal diseases and disorders, for example, IBD, and other colitides using these polypeptides.

The term "MUC" refers to human mucin. The term "Muc" refers to mouse mucin.

Mucin-type proteins represent the major structural proteins of mucous gels that are integral to the epithelial defense of respiratory, digestive, ocular, and reproductive surfaces. The membrane-bound mucins, MUC3, MUC17 (human) and Muc3 (mouse homolog), are highly expressed on the apical surface of normal, healthy intestinal epithelial cells and are thought to play a cytoprotective role in the gut. The extracellular regions of these mucins contain Epidermal Growth Factor (EGF)-like cysteine-rich domains (herein referred to as "CRD1" and "CRD2" as illustrative examples) connected by an intervening linker domain (L). The biological activity of mucins is derived in part from their high molecular weight and structural domains that contain extended highly glycosylated regions and unique globular protein domains.

Previous studies have demonstrated that mouse Muc3 and human MUC3 are highly expressed in the gallbladder, intestine, and colon. These proteins are localized to the cells in the upper villi of the intestine and surface and upper crypt cells of the colon. Muc3 gene expression is up-regulated in small intestinal villi in a mouse model of acute enteritis, and mouse Muc3 and human MUC3A promoter activity can be regulated by cytokines and growth factors, and by hypoxia. The human MUC3 mucin has been shown to be up-regulated in subgroups of human cancers, including lung, renal, breast, gastric and pancreatic cancers. EGF-like regions, also known as G-modules, are common structural features of proteins that participate in protein-protein interactions, including both growth factors and structural proteins. In the intestine, the hormone EGF and related family members have been shown to stimulate cell migration and inhibit apoptosis. Ligand binding to the EGF receptor results in activation of several signaling pathways and a number of target proteins regulating cytoskeletal rearrangement and cellular migration. Although not wishing to be bound by any particular theory, it is believed that MUC17, Muc3 or MUC3 derived polypeptides comprising a CRD domain have biologically active EGF-like modules that may trigger similar pathways as those demonstrated for EGF.

MUC17, Muc3 or MUC3 Derived Polypeptides

Figure 4:
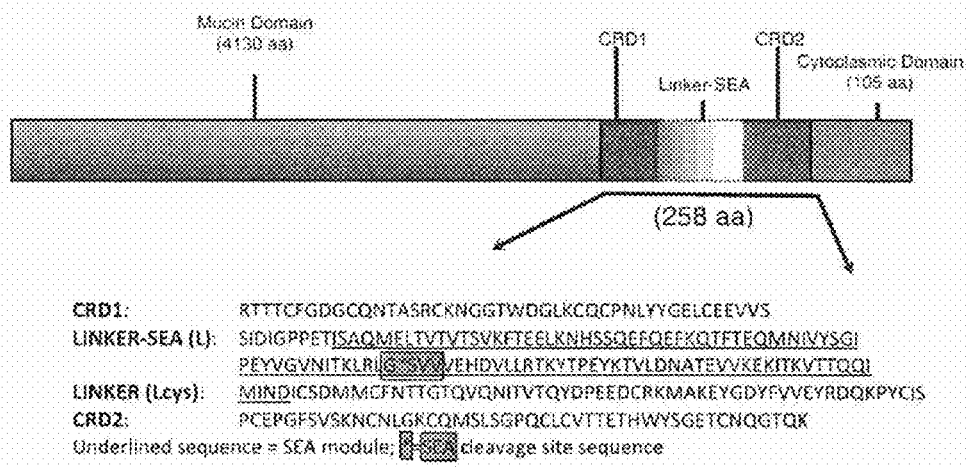

One aspect of the present technology pertains to purified or isolated MUC17, Muc3 or MUC3 derived polypeptides comprising one or more CRD domains (CRD1 and/or CRD2) and a linker domain fragment. In some embodiments, isolated polypeptides derived from MUC17, Muc3 or MUC3 mucin proteins having cytoprotective functions include: MUC17, Muc3 or MUC3 (CRD1-L-CRD2, CRD1-L and L-CRD2) polypeptides, for example, MUC17-derived polypeptides having an amino acid sequence provided in SEQ ID NOs: 1-5. The MUC17, Muc3 or MUC3 derived polypeptides (CRD1-L-CRD2, CRD1-L and L-CRD2) also demonstrate a unique cysteine pattern, as shown in FIGS. 4 & 5.

The term "isolated" or "purified" polypeptide as used herein refers to a polypeptide that has been separated or purified from cellular components that naturally accompany it. Typically, the polypeptide is considered "purified" when it is at least 70% by dry weight (e.g., at least 75%, 80%, 85%, 90%, 95%, or 99% by dry weight) free from the proteins and naturally occurring molecules with which it is naturally associated. Since a polypeptide that is chemically synthesized is, by nature, separated from the components that naturally accompany it, a synthetic polypeptide is "purified." Polypeptides of the present technology can be chemically synthesized, produced recombinantly or can be purified from natural sources (e.g., a biological sample) by known methods such as DEAE ion exchange, gel filtration, and hydroxyapatite chromatography.

The isolated polypeptides of the present technology can also be obtained recombinantly by expressing a nucleic acid in an expression vector, using standard and well-established techniques known in the field of molecular biology. In this regard, the practice of the present technology will employ, unless otherwise indicated, conventional techniques of molecular biology, microbiology, recombinant DNA technology and immunology that are within the skill of those working in the art. Such techniques are explained fully in the literature. Examples of particularly suitable texts for consultation include the following: Sambrook and Russell, *Molecular Cloning; A Laboratory Manual*, Second Edition (1989); *DNA Cloning*, Volumes I and II (D. N Glover ed. 1985); *Oligonucleotide Synthesis* (M. J. Gait ed. 1984): *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the Methods in Enzymology series (Academic Press, Inc.), especially volumes 154 & 155; *Gene Transfer Vectors for Mammalian Cells* (J. H. Miller and M. P. Calos eds. 1987, Cold Spring Harbor Laboratory); *Immunochemical Methods in Cell and Molecular Biology* (Mayer and Walker, eds. 1987, Academic Press, London); Scopes, (1987) *Protein Purification: Principles and Practice*, Second Edition (Springer Verlag, N.Y.); and *Handbook of Experimental Immunology*, Volumes I-IV (D. M. Weir and C. C. Blackwell eds. 1986) which are all incorporated by reference herein in their entireties.

The MUC17, Muc3 or MUC3 derived polypeptides of the present technology can be prepared by any method known in the art, including recombinant DNA-related technologies, biochemical isolation from animal tissue, and chemical synthesis technologies. In particular, a method for making a MUC17, Muc3 or MUC3 derived polypeptide of the present technology includes culturing a host or transgenic cell under conditions in which the nucleic acid or vector is expressed in a suitable host cell, and recovering the MUC17, Muc3 or MUC3 derived polypeptide encoded by the nucleic acid or vector from the host cell or alternatively from the culture. For example, when the vector optionally or preferably expresses the MUC17, Muc3 or MUC3 derived polypeptide or combination of polypeptides as a fusion protein with one or more extracellular or signal-peptide-containing proteins, the recombinant product can be secreted in the extracellular space, and can be more easily collected and purified from the prokaryotic culture medium for further processing, if necessary. Alternatively, the peptide can be harvested from the host cells, or the host cells can be administered directly.

The nucleic acid sequences coding for the MUC17, Muc3 or MUC3 derived polypeptides of the present technology can be inserted and ligated into suitable episomal or non-homologously integrating vectors, e.g., bacterial or viral vectors, which can be introduced in the appropriate host cells by any suitable means (transformation, transfection, conjugation, protoplast fusion, electroporation, calcium phosphate-precipitation, direct microinjection, etc.). In some embodiments, certain well-known factors can be considered when selecting a particular plasmid or viral vector including: the ease of selection of the transformed host cells as opposed to non-transformed host cells; the tropism of the vector towards a desired host cell; the number of copies of the vector which are desired in a particular host; and whether it is desirable to be able to "shuttle" the vector between host cells of different species.

The vector or vectors used should allow the expression of the MUC17, Muc3 or MUC3 derived polypeptides or fusion protein in the prokaryotic or eukaryotic host cells under the control of transcriptional initiation/termination regulatory sequences. These sequences, for example, promoters, can be chosen to be constitutively active or inducible in the chosen host cell. A cell line substantially enriched in such cells can be then isolated to provide a stable cell line. Selection of specific transcriptional initiation/termination regulatory sequences can be made using routine considerations, for example, the eventual host cell in which the expression of the transgene will occur, and other known requirements of the specific vector being employed.

For eukaryotic hosts (e.g., yeasts, insect, plant, or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene that has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells that are stably transformed by the introduced DNA can be selected by introducing one or more markers for example, an antibiotic resistance gene, hygromycin B phosphotransferase gene, neomycin phosphotransferase gene, blasticidin deaminase and the like, allowing the selection of host cells which contain the expression vector. The marker may also provide for prototrophy to an auxotropic host biocide resistance, e.g., antibiotics, or heavy metals such as copper, or the like. The selectable marker gene can either be directly linked to the DNA gene sequences to be expressed, or introduced into the same cell by co-transfection.

Host cells can be either prokaryotic or eukaryotic. Illustrative examples of eukaryotic hosts include mammalian cells, such as human, monkey, mouse, and Chinese Hamster Ovary (CHO) cells. These eukaryotic cells can be advantageous, because they provide post-translational modifications to proteins, including correct folding and glycosylation. A number of recombinant DNA strategies exist that utilize strong promoter sequences and/or high-copy number plasmids to produce the desired proteins in yeast. Yeast-based production of the MUC17 derived polypeptides can be advantageous because in most cases, yeast cells can recognize leader sequences in cloned mammalian gene products and secrete peptides bearing leader sequences (i.e., pre-peptides).

In some embodiments, yeast cells can carry out post-translational peptide modifications including glycosylation and are particularly suitable for large-scale production of the desired MUC17, Muc3 or MUC3 derived polypeptides. In some preferred embodiments, yeast expression plasmids can be constructed using high-copy plasmids with an alpha-mating factor sequence (for secretion). The cDNA for MUC17, Muc3 or MUC3 CRD1-L-CRD2, CRD1-L and L-CRD2 polypeptides can be codon-optimized for high-level expression in yeast. Commercially available high-copy plasmid expression vectors optimized for use with proprietary yeast strains (for example in *S. cerevisiae*) are commercially available from ApoLife (Detroit Mich., USA). The plasmid DNA can be transformed into super-secretory yeast strains that allow secretion of 90% of proteins into media during fermentation. The construct can illustratively also contain a purification or identity tag, for example, a plural histidine (e.g., 6x-His or 8x-His), a Glutathione-S-Transferase (GST), an enzyme or a FLAG tag to simply purification by affinity chromatography, for example, immobilized metal ion affinity chromatography (IMAC). This technique can provide protein of purity ranging from greater than 70%, for example, greater than 70%, or greater than 75%, or greater than 80%, or greater than 85%, or greater than 90%, or greater than 95%, to about 96-100% homogeneous, and if further purification is required ion-exchange and size exclusion chromatography can be employed in combination, methods which are routinely used in the protein purification field.

Several well-established methodologies for preparing specific polypeptides using recombinant DNA technology are available to those skilled in the art. For example, several established books and literature reviews provide teachings on how to clone and produce recombinant proteins using vectors and prokaryotic or eukaryotic host cells, such as some titles in the series "A Practical Approach" published by Oxford University Press (*DNA Cloning 2: Expression Systems*, 1995; *DNA Cloning 4: Mammalian Systems*, 1996; *Protein Expression*, 1999; *Protein Purification Techniques*, 2001).

In addition to isolated MUC17, Muc3 or MUC3 derived polypeptides derived from recombinant methods, the MUC17, Muc3 or MUC3 derived polypeptides can be obtained by chemical synthesis and biochemical isolation from tissue sources known to possess full-length MUC17, Muc3 or MUC3 mucin proteins, which can be manipulated using protease and enzymic digestion to arrive at the subject MUC17, Muc3 or MUC3 derived polypeptides disclosed and exemplified herein. The extent of purity of the MUC17, Muc3 or MUC3 derived polypeptides can be measured using any appropriate method, e.g., column chromatography, polyacrylamide gel electrophoresis, or HPLC analysis.

In some embodiments, the MUC17, Muc3 or MUC3 derived polypeptides of the present technology can be isolated, naturally occurring MUC17, Muc3 or MUC3 mucin proteins modified biochemically to yield polypeptides, for example, as in the case of MUC17, having the amino acid sequence of SEQ ID NOs: 1-5 using established biochemical techniques published in biochemical journals, for example, Carraway, K. L. "Preparation of Membrane Mucin", *Methods in Molecular Biology*, Vol. 125, *Glycoprotein Methods and Protocols—The Mucins*, ed. Anthony P. Corfield (2000) the disclosure pertaining to purification of mucins being incorporated herein by reference in its entirety. Alternatively, recombinant methods for producing the isolated MUC17, Muc3 or MUC3 derived polypeptides can be adapted from those methods described in S. B. Ho et al., "Cysteine-rich domains of muc3 intestinal mucin promote cell migration, inhibit apoptosis, and accelerate wound healing", *Gastroenterology* 131 (2006), 1501-1517, and L. L. Shekels et al., "Biological activity of the human MUC17 membrane-bound mucin cysteine-rich domain", *Gastroenterology* 132 (2007) A569, which are incorporated herein by reference in their entireties.

In some embodiments, the skilled artisan will further appreciate that changes can be introduced into a nucleic acid molecule (e.g., those encoding MUC17, Muc3 or MUC3 derived polypeptides, for example, those MUC17 derived polypeptide amino acid sequences provided in SEQ ID NOs: 1-5, as discussed herein, thereby leading to changes in the amino acid sequence of the encoded MUC17, Muc3 or MUC3 derived polypeptides. In one example, changes can be introduced into MUC17, Muc3 or MUC3 polypeptide encoding nucleic acid coding sequences leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of Protein Sequence and Structure*, Vol. 5, Suppl. 3, pp 345-352) provides frequency tables for amino acid substitutions that can be employed as a measure of amino acid similarity. A non-conservative substitution is one in which an amino acid residue is replaced with an amino acid residue that does not have a similar side chain.

The present technology also provides for chimeric or fusion polypeptides. As used herein, a "chimeric" or "fusion" polypeptide includes one or more MUC17, Muc3 or MUC3 derived polypeptides operatively linked to a heterologous polypeptide. A heterologous polypeptide can be linked at either the N-terminus, C-terminus or at some location between the N and C-termini of the MUC17, Muc3 or MUC3 derived polypeptides, e.g., CRD1-L-CRD2, CRD1-L, or L-CRD2 polypeptides. In some embodiments, the fusion or chimeric protein can include: a full or partial mucin protein that is naturally expressed in human or animal tissues, including those from human mucins and mouse mucins (e.g., MUC1, MUC2, MUC3, MUC4, MUC5AC, MUC5B, MUC6, MUC7, MUC8, MUC9, MUC10, MUC11, MUC12, MUC13, MUC15, MUC16, MUC17, MUC18, MUC19, and MUC20). Within a chimeric or fusion polypeptide, the term "operatively linked" is intended to indicate that the two polypeptides are encoded in-frame relative to one another. In a fusion polypeptide or protein, the heterologous polypeptide generally has a desired property such as the ability to purify the fusion polypeptide (e.g., by affinity purification). In some embodiments, the presence of the heterologous polypeptide does not alter the function and/or activity of the MUC17, Muc3 or MUC3 derived polypeptides.

A chimeric or fusion polypeptide of the present technology can be produced by standard recombinant DNA techniques and can use commercially available constructs.

In some embodiments, a fusion protein of a MUC17, Muc3 or MUC3 derived polypeptide can also include a heterologous polypeptide commonly used in purification, isolation and activity assays, for example, a glutathione S-transferase (GST) tag, 6×-His or 8×-His tags, and a FLAG-tag, among others. In addition, a proteolytic cleavage site can be introduced at the junction between a MUC17, Muc3 or MUC3 derived polypeptide and a non-MUC17, Muc3 or MUC3 derived polypeptide fusion partner to enable separation of the two polypeptides subsequent to purification of the fusion protein. Enzymes that cleave such proteolytic sites include Factor Xa, thrombin, or enterokinase. Representative expression vectors encoding a heterologous polypeptide that can be used in affinity purification of a MUC17, Muc3 or MUC3 derived polypeptide include pGEX (Pharmacia Biotech Inc; Smith & Johnson, 1988, Gene, 67:31-40), pMAL (New England Biolabs, Beverly, Mass.) and pRIT5 (Pharmacia, Piscataway, N.J. USA). In some embodiments, the MUC17, Muc3 or MUC3 derived polypeptides of the present technology can also be purified using recombinant techniques that have a multi-Histidine (e.g., 6×-His) or GST or FLAG tag to facilitate purification and handling. In some embodiments, in addition to the fusion proteins described above, the fusion proteins of the present technology can also include a MUC17, Muc3 or MUC3 derived polypeptide and a detection marker, for example: a biotin/avidin/streptavidin marker; a S-protein marker; a fluorescence marker, for example, a green fluorescence protein (GFP and EGFP), a red fluorescence protein (DsRed or drFP583); a chemiluminescence marker; a detectable enzyme, for example, glucose oxidase, alkaline phosphatase and horse radish peroxidase enzyme markers, among other detectable markers and combinations thereof.

Methods for Assaying the Activity of Isolated MUC17, Muc3 or MUC3 Derived Polypeptides In some embodiments, the MUC17, Muc3 or MUC3 derived polypeptides can be assayed for activity using several activity assays. In one illustrative example, cell migration assays can be used to determine whether the isolated MUC17, Muc3 or MUC3 derived polypeptide possesses activity. In an illustrative embodiment, confluent 24-well plates of A431 or LoVo cells are serum-starved overnight. The medium can then be replaced with PBS and the monolayers can be mechanically wounded using a single-edged razorblade. After wounding, cells are rinsed twice with PBS and incubated with one or more MUC17, Muc3 or MUC3 derived polypeptides of interest in DMEM for 18 to 24 h (37° C., 5% $CO_2$, 0% FCS). After fixation and staining, those cells that have migrated across the wounded edge are counted at 100× using an inverted light microscope. Two successive fields can be counted and averaged within one well, and three to twelve wells averaged for each condition in each experiment.

In some embodiments, young adult male colonic (YAMC) cells are conditionally immortalized mouse colon cells that can be grown to confluency and then a rotating disc can be used to scrape cells from an area within a 24 well plate. After 20 hours, the area of wound remaining can be measured in the presence and/or absence of the MUC17, Muc3 or MUC3 derived polypeptide or nucleic acid encoding the same under investigation.

Other methods for determining the activity of a MUC17, Muc3 or MUC3 derived polypeptide can also include methods for determining the ability of the polypeptide to inhibit cellular apoptosis. Apoptosis can be induced using the extrinsic receptor mediated agents TNF-alpha (used at 100 ng/mL, Sigma, St. Louis, Mo.) and interferon gamma (100 ng/mL×24 hrs) followed by anti-fas (500 ng/mL for 48 hours, R&D Systems) and by intrinsic or direct interference with DNA synthesis using 5-fluorouracil (SFU, Sigma, 100 μg/mL×24 hours). Apoptosis can be determined using the nuclear dye, Hoechst 33258 (Polysciences Inc., Warrington, Pa.) and fluorescent imaging to identify apoptotic nuclei by morphology. Apoptosis can be measured in histologic specimens using a terminal deoxynucleotidyl transferase-mediated deoxyuridine triphosphate biotin nick-end labeling (TUNEL) assay (TACS.XL In Situ Apoptosis Detection Kit, R&D Systems, Minneapolis, Minn.), according to the manufacturer's directions.

In another example, the activity of MUC17, Muc3 or MUC3 derived polypeptides can be assayed using cell proliferation assays. For these kinds of activity assays, cells obtained from a mammalian cell line can be cultured in 24-well plates until 60% confluent and then switched to media containing 0.5% serum for 24 h. The monolayers can be rinsed with PBS followed by incubation with the candidate MUC17-derived polypeptide of interest in DMEM for 24 hr. Cells can be quantitated by trypan blue staining or any other appropriate cell-counting system used in the art, for example, FACS cytometry and the like. To get statistically reliably cell counts, two counts can be averaged from each well and six wells averaged per treatment. Proliferation for each treatment can be represented as a percentage relative to the serum-free control.

In some embodiments, the activity of the MUC17, Muc3 or MUC3 derived polypeptides of the present technology can be confirmed by a positive cell-migration assay and/or inhibition of cellular apoptosis, in addition to cell inactivity towards EGF receptors.

In some embodiments, the activity of a MUC17, Muc3 or MUC3 derived polypeptide can be determined and confirmed using animal-model studies of colitis. In some examples, the animal models useful in the determination of efficacy can include established mouse models of colitis. Methods for testing MUC17, Muc3 or MUC3 derived polypeptides, i.e., MUC17, Muc 3 and MUC3 CRD1-L-CRD2, CRD1-L and L-CRD2 polypeptides in a mouse model of colitis can involve the determination of accelerated healing of acetic acid- and/or dextran sodium sulfate-induced colitis. Other known animal model of colitis can be used to test the activity of the MUC17, Muc3 or MUC3 derived polypeptides of the present technology, for example, chemically induced mouse models of IBD. These can include IBD induction in murine models with the chemical agents trinitrobenzene sulfonic acid (TNBS), and oxazolone, and can include acute or chronic dextran sodium sulfate (DSS) colitis models. See Waldner, M. J. et al., *Curr. Protoc. Pharmacol.* (2009), 46:5.55.1-5.55.15.

Pharmaceutical Compositions

MUC17, Muc3 or MUC3 derived polypeptides and/or pharmaceutically acceptable salts thereof, can be used in pharmaceutical compositions of the present technology (e.g., a MUC17, Muc3 or MUC3 derived polypeptide containing a Linker domain and at least one CRD domain and/or nucleic acid molecules encoding a MUC17, Muc3 or MUC3 derived polypeptide). The one or more MUC17, Muc3 or MUC3 derived polypeptides can be incorporated into a pharmaceutical composition suitable for administration to cure, treat or prevent a gastrointestinal disease or related symptoms. Such compositions typically comprise a MUC17, Muc3 or MUC3 derived polypeptide and/or a nucleic acid molecule encoding the same, and a pharmaceutically acceptable carrier, diluent or excipient. As used herein, "pharmaceutically acceptable carrier, diluent or excipient" is intended to include any and all solvents, dispersion media, coatings, antibacterial and antifungal agents, isotonic and absorption-delaying agents, and the like, that are compatible with pharmaceutical administration. The use of such media and agents for pharmaceutically active substances is well-known in the art. Except insofar as any conventional media or agent is incompatible with the active MUC17, Muc3 or MUC3 derived polypeptide, the carrier, diluent or excipient, use thereof of such media or agents in the pharmaceutical composition is contemplated.

A pharmaceutical composition of the present technology can be formulated to be compatible with its intended route of administration, as determined by those of skill in the art, and optionally, formulated under FDA-approved methods. Examples of routes of administration of MUC17, Muc3 or MUC3 derived polypeptides and/or nucleic acids encoding the same, can include: parenteral, e.g., intravenous, intradermal, subcutaneous; oral (e.g., ingestion or inhalation); transdermal (topical), transmucosal; and rectal administration. Solutions or suspensions used for parenteral, intradermal, or subcutaneous application can include the following components: a sterile diluent such as water for injection, saline solution (e.g., phosphate buffered saline (PBS)), fixed oils, a polyol (for example, glycerol, propylene glycol, and liquid polyethylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampoules, disposable syringes or multiple dose vials made of glass or plastic.

Oral compositions generally include an inert diluent or an edible carrier. Oral compositions can be liquid, or can be enclosed in gelatin capsules or compressed into tablets. Pharmaceutically compatible binding agents, and/or adjuvant materials can be included as part of an oral composition. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Transmucosal administration can be accomplished through the use of nasal sprays or suppositories. For transdermal administration, the active compounds are formulated into ointments, salves, gels, or creams as generally known in the art.

In some embodiments, rectal administration of the MUC17, Muc3 or MUC3 derived polypeptide and/or polynucleotide composition or pharmaceutical preparation can be achieved using any commonly accepted dose and formulation, and method of administration, e.g., via suppositories, enemas and the like, and other perianally suitable methods.

It is especially advantageous to formulate oral, parenteral or rectal compositions in dosage unit form for ease of administration and uniformity of dosage. A "dosage unit form" as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the present technology are dependent upon the amount of a compound necessary to therapeutically treat the individual. The amount of a compound necessary can be formulated in a single dose, or can be formulated in multiple dosage units. Treatment of an individual may require a one-time dose, or may require repeated doses.

For therapeutically effective compositions, the dose of MUC17, Muc3 or MUC3 derived polypeptide and/or polynucleotide encoding the same can range from about 0.01 to about 100 mg/kg body weight/day, from about 0.01 to about 50 mg/kg body weight/day, from about 0.01 to about 30 mg/kg body weight/day, from about 0.01 to about 10 mg/kg body weight/day, (generally, from about 0.5 mg/kg to about 5 mg/kg body weight). Modifications such as lipidation (Cruikshank et al., 1997, *J. Acquired Immune Deficiency Syndromes and Human Retrovirology*, 14:193) can be used to stabilize polypeptides and to enhance uptake and tissue penetration. For nucleic acids encoding the MUC17, Muc3 or MUC3 derived polypeptides of the present technology, the dose of nucleic acid administered will depend on several well-known factors associated with nucleic acid delivery in vivo, such as, the level of expression of the expression vector and the route of administration. In some embodiments, the route of administration for nucleic acids encoding MUC17, Muc3 or MUC3 derived polypeptides can include oral, systemic injection, stereotactic administration into a lesion or other area of epithelial cell damage, and combinations thereof. Methods for encapsulating nucleic acids for parenteral or oral administration are well-known in the art of nucleic acid administration. Preferably, the amount of vector that encodes a therapeutically effective amount of a MUC17, Muc3 or MUC3 derived polypeptide (e.g., from about 0.1 mg/kg to about 100 mg/kg of body weight) is administered to an individual in need of therapy.

Methods of Using MUC17, Muc3 or MUC3 Derived Polypeptides

The present technology has identified MUC17, Muc3 or MUC3 derived polypeptides that are not up-regulated in carcinomas and provide cytoprotective functions in the intestinal tract. Use of isolated MUC17, Muc3 or MUC3 derived polypeptides for mucosal restitution may potentially augment current therapies for IBD, be part of a combination treatment in admixture with a second active agent, or act as a novel stand alone agent.

The present technology provides methods for preventing or treating a disease of the gastrointestinal tract in an individual who has or is at risk of developing a disease of the gastrointestinal tract. The present technology also provides methods for treating an epithelial lesion in an individual. Individuals are treated by administering a composition to an individual, the composition containing MUC17, Muc3 or MUC3 derived polypeptides i.e. CRD1-L-CRD2, and/or CRD1-L, and/or L-CRD2 polypeptides, or one or more nucleic acids encoding such polypeptide or polypeptides, in admixture with at least one pharmaceutically acceptable excipient. In some embodiments, the composition can include one or more of the polypeptides described herein in admixture with at least one pharmaceutically acceptable carrier or diluent, for example, those commonly used to provide oral, parenteral, rectal, and other methods of administration that are commonly used to treat the particular gastrointestinal disease or disorder illustrated herein. Individuals at risk for a disease of the gastrointestinal tract can be administered the polypeptide or nucleic acid of the present technology prior to the manifestation of symptoms that are characteristic of a disease or condition of the gastrointestinal tract, such that the disease or condition is prevented or delayed in its progression, and/or severity.

Without wishing to be bound by any particular theory, it is believed that cell migration and apoptosis are critical for normal intestinal homeostasis and for mucosal healing in response to injury. The normal intestinal barrier is maintained by the continuous migration of cells from the proliferative compartment in the lower crypts to the intestinal villi or colon surface. Following intestinal injury, the ability of cells to migrate and close a wound allows for restitution of the epithelial barrier more rapidly than by enhanced proliferation. Increased cell migration occurs in response to experimental intestinal injury and peptic ulcer disease, as well as inflammatory diseases of the bowel. Increased cell migration and anti-apoptosis are often associated and share some common pathways. Thus, the MUC17, Muc3 or MUC3 derived polypeptides of the present technology that enhance intestinal cell migration, inhibit or reduce apoptosis and are therapeutic for conditions of epithelial injury, including, lesions of the upper alimentary canal, the esophagus, the dermis, the epidermis, the vagina, the cervix, the uterus, the intestinal areas of the duodenum, jejunum, and ileum, the large intestine, the distal bowel, the respiratory epithelium, or the corneal epithelium, are thus considered therapeutically effective.

Illustrative embodiments of kinds of epithelial lesions that can be treated, cured, or prevented by the compositions of the present technology can include: stomatitis, mucositits, gingivitis, a lesion caused by gastro-esophageal reflux disease, a traumatic lesion, a burn, a pressure ulcer, eczema, contact dermatitis, psoriasis, a herpetic lesion, acne, enteritis, proctitis, a lesion caused by Crohn's disease or ulcerative colitis, keratitis, a corneal ulcer, keratoconjunctivitis, a keratoconus, a conjunctiva, ocular inflammation, or a cicatricial penhigoid. By way of example, a lesion as described herein can be caused by a bacterial, viral, protozoan, or fungal infection; by an allergic reaction, by an inflammatory response, an autoimmune response, asthma, chronic obstructive pulmonary disease; by the inhalation of smoke, particulate matter, or a chemical; or by anti-neoplastic chemotherapy or anti-neoplastic radiation therapy.

Illustrative diseases or disorders of the gastrointestinal tract that can be treated, cured, or prevented with the compositions of the present technology, include, but are not limited to, epithelial lesions, irritable bowel disease, ulcerative colitis, mucositis, Crohn's disease, chronic colitis, microscopic colitis, indeterminate colitis, ileal inflammation and diverticulitis.

In one embodiment, an active agent administered to an individual can include a MUC17, Muc3 or MUC3 derived polypeptide (e.g., MUC17, Muc3 or MUC3 CRD1-L-CRD2, and/or CRD1-L, and/or L-CRD2 polypeptides; e.g., polypeptides having an amino acid sequence as shown in SEQ ID NOs: 1, 2, 3, 4, and/or 5). An active agent for administration can be a fusion polypeptide comprising a MUC17, Muc3 or MUC3 derived polypeptide. In another embodiment, an active agent administered to an individual can be a nucleic acid molecule encoding a MUC17, Muc3 or MUC3 derived polypeptide, e.g., one or more of MUC17 CRD1-L-CRD2, CRD1-L, and L-CRD2 polypeptides. Nucleic acid coding sequences (e.g., full-length or otherwise) can be introduced into an appropriate expression vector such that a MUC17, Muc3 or MUC3 derived polypeptide or fusion protein can be produced upon appropriate expression of the expression vector within the transformed or transfected cells or tissue.

Additional and/or complimentary active compounds can also be incorporated into the compositions of the present technology to treat a disease and/or disorder of the gastrointestinal tract. For example, additional or secondary active agents that are well known in the treatment of IBD and other colitides can be included in the pharmaceutical composition, i.e., a single-unit dose with one or more MUC17, Muc3 or MUC3 derived polypeptides and/or nucleic acids encoding the same and one or more additional or secondary active agents or the additional active agent(s) may be part of a separate pharmaceutical composition. For combination treatment with more than one active agent where the active agents are in separate dosage formulations, the active agents may be administered separately or in conjunction. In addition, the administration of one agent may be prior to, concurrent to, or subsequent to the administration of the other agent.

When co-administered with other agents, e.g., when co-administered with a pain or inflammation medication, an "effective amount" of the second or additional agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, MUC17, Muc3 or MUC3 derived polypeptides described herein can be administered to a subject in need thereof in a dosage range from between about 0.01 to about 100 mg/kg of body weight/day, from about 0.01 to about 50 mg/kg body weight/day, from about 0.01 to about 30 mg/kg body weight/day, from about 0.01 to about 10 mg/kg body weight/day, and preferably, from about 0.5 mg/kg to about 5 mg/kg body weight.

When "combination therapy" is employed, an effective amount can be achieved using a first amount of a MUC17, Muc3 or MUC3 derived polypeptide or polynucleotide encoding the same described herein or a pharmaceutically acceptable salt, solvate (e.g., hydrate), co-crystal or pro-drug thereof and a second amount of an additional suitable therapeutic agent (e.g., an agent to treat pain, inflammation or infection of the epithelial tissue leading to the diseases and disorders described herein).

In some embodiments of the present technology, the MUC17, Muc3 or MUC3 derived polypeptides and/or polynucleotides encoding the same described herein, and, in some embodiments, one or more additional therapeutic agents are each administered in an effective amount (i.e., each in an amount which would be therapeutically effective if administered alone). In other embodiments, the MUC17, Muc3 or MUC3 derived polypeptides and/or polynucleotides encoding the same described herein, and the one or more additional therapeutic agents, are each administered in an amount which alone does not provide a therapeutic effect (a sub-therapeutic dose). In yet other embodiments, the MUC17, Muc3 or MUC3 derived polypeptides and/or polynucleotides encoding the same described herein can be administered in an effective amount, while the one or more additional therapeutic agents are administered in a sub-therapeutic dose. In still other embodiments, the MUC17, Muc3 or MUC3 derived polypeptides and/or polynucleotides encoding the same described herein can be administered in a sub-therapeutic dose, while the one or more additional therapeutic agents, for example, a suitable inflammation modulating-therapeutic agent, is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, a capsule or tablet having a fixed ratio of first and second amounts, or in multiple, separate capsules or tablets for each. In addition, such co-administration also encompasses use of each MUC17, Muc3 or MUC3 derived polypeptide and polynucleotide encoding the same in a sequential manner in either order. When co-administration involves the separate administration of the first amount of a MUC17, Muc3 or MUC3 derived polypeptide and/or polynucleotide encoding the same described herein and a second amount of an additional therapeutic agent, the active agents are administered sufficiently close in time to have the desired therapeutic effect. For example, the period of time between each administration that can result in the desired therapeutic effect, can range from minutes to hours and can be determined taking into account the properties of each compound such as potency, solubility, bioavailability, plasma half-life and kinetic profile. For example, a compound described herein and a second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as one or more MUC17, Muc3 or MUC3 derived polypeptides and/or polynucleotides encoding the same described herein) can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second active agent) to a subject.

In some embodiments, the additional or second active agent can include one or more of: aminosalicylates (such as aulfasalazine (Azulfidine), aesalamine (Asacol, Rowasa)), acetaminophen, laxatives, non-steroidal anti-inflammatory drug substances (NSAIDS), antibiotics commonly administered for gastrointestinal diseases such as Crohn's Disease (for example, metronidazole and ciprofloxacin), corticosteroids, anti-diarrheals and immune modifying agents (e.g., immuno-suppressants, for example, azathioprine (Imuran), mercaptopurine (Purinethol), adalimumab (Humira), infliximab (Remicade), certolizurnab pegol (Cimzia), methotrexate (Rheumatrex), cyclosporine (Gengraf, Sanimmune and Neoral) and natalizumab (Tysabri)).

EXAMPLES

Example 1

MUC17 Derived Polypeptides and Activity

In FIG. 1, amino acid sequences of MUC17 derived polypeptides of embodiments of the present invention are provided. CRD1-L-CRD2 has the amino acid sequences of SEQ ID NOs: 1 and 2, with the addition of a serine at the C-terminal in SEQ ID NO: 2. CRD1-L polypeptide has the amino acid sequence of SEQ ID NO: 3. L-CRD2 polypeptide has the amino acid sequences of SEQ ID NOs:4 and 5, with the addition of a serine at the C-terminal in SEQ ID NO: 5.

Figure 2:
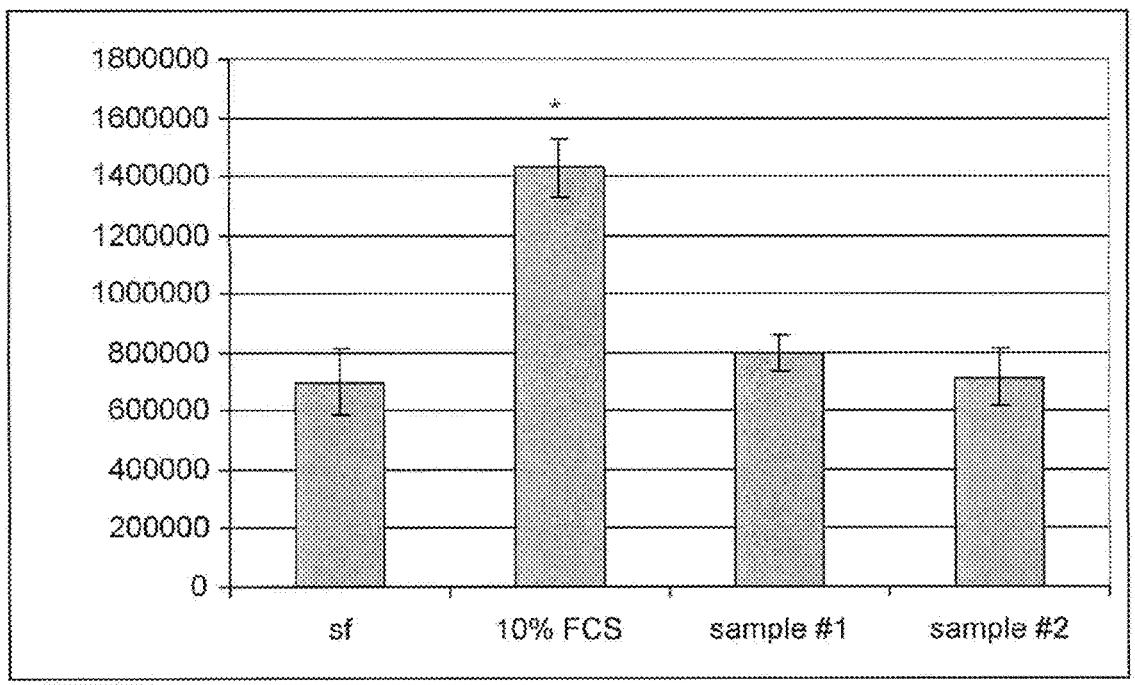
FIG. 2 depicts a graph representing the efficacy of His-MUC17-L-CRD2 samples to induce cellular proliferation when compared to positive control 10% Fetal Calf Serum (FCS) and negative control serum free (SF) media samples in vitro.

The L-CRD2 polypeptide of the present technology has shown activity in various assays described herein when compared for example to CRD1-L-CRD2. For example, in a cell proliferation assay, conducted essentially as described above, L-CRD2 polypeptide administered in amounts of 10 μg/mL showed no statistically significant inducement of cellular proliferation of LoVo cells in vitro, especially when compared to 10% FCS, and was comparable to negative control serum-free media (see FIG. 2). This non-proliferative property of L-CRD2 lends itself to being an ideal candidate for treatment of gastrointestinal disease and disorders without the danger of hyperplasia or tumorigenesis of surrounding cells.

Figure 3:
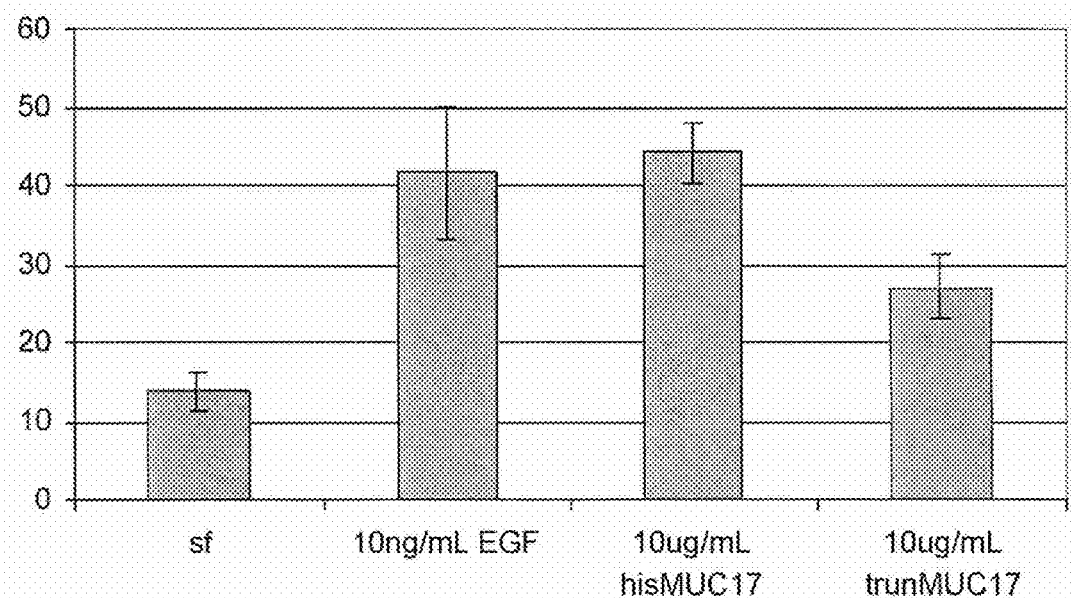
FIG. 3 depicts a graph representing the efficacy of His-MUC17-L-CRD2, His-MUC17 CRD1-L-CRD2, EGF and serum-free media to induce cell migration of LoVo cells in vitro.

In FIG. 3, experimental results are shown indicating that L-CRD2 polypeptide possesses mucin-like promotion of cell migration. LoVo cells were incubated in tissue culture media in the absence of serum, in the presence of EGF, His-tagged MUC17 protein, and His-tagged L-CRD2 polypeptide derived from MUC17 ("truncated" or "trunMUC17"). The results show a statistically significant induction of cellular migration when compared to serum-free media. L-CRD2 was shown to provide the necessary signals to LoVo cells to induce cell migration, a hallmark activity known to be related to tissue healing and cytoprotective function.

Example 2

Recombinant Proteins

FIGS. 4 and 5A-5B depict the structure and amino acid sequences of recombinant proteins synthesized to test the effectiveness of peptide embodiments of the present technology.

In FIGS. 5A-5B, underlined residues indicate SEA (sea-urchin sperm protein, enterokinase and agrin), and shaded regions indicate the SEA cleavage site. FIG. 5A: (1) Mouse Muc3 CRD-L-CRD2-His$_8$, (1-1 through G-266) containing a C-terminal 8-His tag; lowercase: residues from the pre-CRD1 domain. (2) Mouse Muc-3 CRD1-(11 amino acid spacer)-L-Cys domain-CRD2; lowercase: pre-CRD1 sequence, parenthesis: 11-residue spacer region (followed by the L-Cys domain of Muc 3). (3) Mouse Muc3 CRD1-(20 amino acid spacer)-L-Cys domain-CRD2, which is the same as in (2) above, except: parentheses: 20-residue space region, contains 20 amino acids, underline: partial SEA sequence region. FIG. 5B: (4) Linker domain-SEA module Muc3, with the Linker region pre-CRD2 Cys-containing region (L-Cys) lacking; underline: the Muc3 SEA module, shading: SEA cleavage site. (5) Human GST-MUC17CRD1-Linker-CRD2 (R-1 through S-260). (6) Human MUC17CRD1-Linker-CRD2 (R-1 through K-259); lowercase: 5-residue extension, followed by a C-terminal 8-His tag. (7) Full-length sequence of MUC17 CRD1-L-CRD2 as expressed in baculovirus-insect cell system, which begins with a portion of the pBAC vector remaining after removal of the gp64 signal peptide during secretion, this vector portion having a His$_6$ tag, and sites for cleavage by thrombin and enterokinase, and this extra segment is present in the MUC17 derived from insect cells; brackets: part of the expression vector.

Synthesis of His-tagged fusion proteins: The mouse Muc3CRD1-L-CRD2 DNA fragment (FIG. 5A, (1)) was cloned into pET28a vector, sequenced, and transformed into BL21(DE3) cells. This sequence expresses a Muc3CRD1-L-CRD2 protein with a C-terminal $His_8$ tag. Freshly transformed cells were inoculated and grown overnight in 5 mL of LB+100 µg/mL kanamycin then induced with 1 mM IPTG (isopropylthio-beta-D-galactoside (IPTG; Fisher, Pittsburgh, Pa.). Induced cells were collected by centrifugation and lysed by sonication in L buffer (50 mM Tris (pH 8.0), 100 mM NaCl, 5 mM EDTA, 0.5% (v:v) Triton-X-100, 0.1% (v:v) 2-ME (beta-mercaptoethanol), 100 µM PMSF). The lysate was centrifuged and the insoluble fraction (inclusion bodies) was washed in L buffer. The resultant insoluble protein was resuspended in PS buffer (50 mM $Na_{241}PO_4$, pH 7.6, containing 100 mM NaCl) by sonication and then dissolved with the addition of urea to 6 M (PSU buffer). The solubilized protein was next purified by binding to PSU equilibrated Ni-NTA resin and eluted with PSU+0.5 M imidizole. The protein was refolded by dialyzing in a 5 kDa MWCO membrane against 100 volumes of 50 mM Tris (pH 8.2) and 137 mM NaCl with three changes of buffer. Mouse Muc3 CRD1-L-CRD2 coding region was amplified and subcloned with part of the L region deleted, specifically most of the SEA module including the cleavage site, and replaced by a coding region for 11 random amino acids (FIG. 5A, (2)), or for 20 random amino acids (FIG. 5A, (3)), or for the Linker-SEA domain only without the L-Cys region (FIG. 5A (4)). The PCR products were topo-cloned into pCR2.1 142 and sequenced. These Muc3-CRD1-(11 aa spacer-L-Cys)-CRD2, Muc3 (CRD1-(20aa spacer-L-Cys)-CRD2, and Muc3 (L without L-Cys) coding sequences were subcloned into pET23a using NdeI and HindIII. These sequences express the proteins with a C-terminal $His_8$ tag and were transformed into BL21 (DE3) cells. Freshly transformed cells were inoculated and grown overnight in 5 mL of LB+100 µg/mL ampicillin, induced with 1 mM IPTG, and the cells were processed as described above. Similarly, the MUC17-CRD1-L-CRD2 coding region was amplified and the PCR product was topo-cloned into pCR2.1 and sequenced. The MUC17-CRD1-L-CRD2 coding sequence was subcloned into pET28a using NcoI and XhoI to create pET28 Muc17. This sequence expresses MUC17-CRD1-CRD2 with a C-terminal $His_8$ tag. (FIG. 5B (6)) This plasmid was transformed into BL21(DE3) and the bacteria processed as described above.

Example 3

GST-Fusion Proteins

The extracellular, globular region of mouse Muc3 including both EGF-like domains (Muc3CRD1-L-CRD2, previously labeled m3EGF1,2) was amplified from mouse intestinal cDNA. The resulting fragments were cloned into the pGEX-2TK vector (Amersham, Piscataway, N.J.), sequenced, and introduced into E. coli strain BL21 (Invitrogen, Carlsbad, Calif.). GST-fusion protein were expressed in E. coli by induction with 0.5 mM IPTG and purified by affinity chromatography using glutathione agarose (Sigma Chemical Co, St. Louis, Mo.). Similarly, the Muc17-CRD1-L-CRD2 coding region was amplified from human intestinal cDNA, cloned into the pGEX-2TK vector (Amersham, Piscataway, N.J.), sequenced, and introduced into the E. coli BL21 strain. GST-fusion proteins (FIG. 5B (5)) were then expressed in E. coli by induction with 0.5 mM isopropylthio-beta-D-galactoside and purified by affinity chromatography using glutathione agarose (Sigma Chemical Co, St. Louis, Mo.). The yield of proteins synthesized in E. coli ranged from 40 to 50 mg/L and were calculated to be about 90% pure based on Coomassie blue staining following reducing SDS-PAGE, with an approximate molecular weight of 55-72 kDa (GST-tagged Muc3 and MUC17 CRD1-L-CRD2) and 30-35 kDa (His-tagged Muc3 and MUC17 CRD1-L-CRD2) (data not shown).

Example 4

Baculovirus-Insect Recombinant Proteins

Proteins produced as inclusion bodies in E. coli require dissolution under denaturing conditions and refolding to yield protein soluble in physiological buffers. In order to assure that the His-tagged MUC17-CRD1-L-CRD2 was in a native conformation, the protein was produced in insect cells. The sequence was cloned into the transfer vector pBac3 (Novagen) and co-transfected into Sf9 insect cells with baculovirus DNA. The MUC17-CRD1-L-CRD2 gene isolated from the E. coli vector was cloned as a HindIII/XhoI fragment. The gene already had a carboxy terminal $His_8$ tag identical to what was expressed in E. coli. Transcription starts with the methionine of the gp64 signal peptide. During secretion, the gp64 signaling peptide is cleaved, leaving a portion of the pBAC vector in the final protein. Notable features encoded 5' to the gene include: (1) an N-terminal $His_6$ tag, (2) an N-terminal S-tag (both used for purification), (3) a thrombin cleavage site and (4) an enterokinase cleavage site. His-tagged protein was then purified by immobilized metal-ion affinity chromatography (IMAC) and dialyzed into PBS. The protein was secreted and purified from cell supernatant. The sequence expressed is given in (FIG. 5B (7)). The protein was ~95% pure based on SDS-PAGE analysis and N-terminal sequencing (FIG. 10). In addition, recombinant proteins were endotoxin-purified using Detoxi-Gel Endotoxin Removal Gel (Pierce, Rockford, Ill.), which did not alter the activity of the proteins.

Example 5

Cell Lines and Cell Culture

Several types of colonic cells lines were used for these experiments. LoVo cells are a human colon cancer cell line known to respond to Muc3 CRD polypeptide, and express ErbB1 and low level ErbB2 receptors. Colon cell lines commonly used as models of "normal" colon cells were used, including the rat intestinal cell line IEC-6 (American Type Culture Collection (Manassas, Va.) and the Young Adult Mouse Colon (YAMC) cell line. YAMC are conditionally immortalized mouse colon cells grown in RPMI 1640 supplemented with 5% FCS+50 U penicillin/mL and 0.05 µg streptomycin/mL. YAMC cells have previously been shown to respond to Muc3 CRD protein and are known to express EGF-type receptors. Cells were grown in 24-well plates for cell migration and proliferation experiments or T-25 flasks for immunoblotting experiments. LoVo and IEC-6 cells were grown using DMEM supplemented with 10% fetal calf serum+50 U 219 penicillin/mL and 0.05 µg streptomycin/mL (Invitrogen, Carlsbad, Calif.). Cells were cultured at 37° C., 5% $CO_2$, 10% FCS until the desired confluence was reached. The monolayers were washed with PBS for 24 hr before experiments and switched to serum-free media for cell migration and immunoblotting experiments.

Example 6

SDS-PAGE and N-terminal Sequencing

After quantification by DC Protein Assay (Bio-Rad, Hercules, Calif.) equal amounts of total protein were resolved by 10% SDS-PAGE. Automated Edman degradation was performed with the aid of an Applied Biosystems Model 494 Protein Sequencer (Foster City, Calif.) fitted with an HPLC system for analysis of PTH amino acids.

Example 7

Cell Proliferation

Cells in triplicate were seeded into 24-well plates, exposed to media with and without serum and/or recombinant proteins. The cells were subsequently trypsinized at various time points and counted using a hemocytometer.

Example 8

Cell Migration (Wound Healing) Assay

Cells were seeded onto 6-well plates, coated with poly-L-lysine, and cultured until confluent. When cells were 90% confluent, an area of cells was scraped with a razor, producing a sharp, clean scrape. Several scrapes were made per well. Cells surrounding the scrape were allowed to migrate over the scrape over 48 h in complete media. Cells were then fixed and stained with Dip Quick (Jorgensen Laboratories, Loveland, Colo.). The number of cells that migrated across the scrape was counted at 400× magnification. For inhibition experiments, cells were pretreated with the ERK inhibitor, U0126 (Calbiochem, San Diego, Calif.), when indicated, for 1 hr in fresh media followed by treatment with recombinant proteins.

Example 9

Apoptosis

Apoptosis was induced by incubating cells with either interferon gamma at 100 ng/mL for 24 h followed by removal of the interferon and the addition of anti-Fas antibody at 500 ng/mL for 48 h (R&D Systems, Minneapolis, Minn.), or 125 µM etoposide (Calbiochem, San Diego, Calif.). LoVo cells were previously shown to be sensitive to anti-Fas treatment. Cells were pretreated with or without recombinant proteins 1 hr prior to addition of anti-Fas. Cells were fixed in 4% paraformaldehyde in PBS pH 7.4 for 5 min, then washed twice in PBS. The cells were stained with the nuclear dye, Hoechst 33258 (Polysciences Inc., Warrington, Pa.), at a concentration of 5 µg/mL in PBS for 30 min, rinsed, coverslipped with Slowfade Antifade (Molecular Probes, Eugene, Oreg.), and then immediately imaged using an ultraviolet microscope. Apoptotic nuclei were identified by morphology. The total number of normal and apoptotic nuclei was counted in three 400× lens fields per dish (representing N200 nuclei per dish). Three or more dishes were used for each experimental condition. Data are also represented as normalized to control with anti-Fas in order to compare experiments done at different times with variations in the maximal apoptosis observed with control anti-Fas (range 14-28%).

Example 10

Statistical Analysis

Data were tested for normality using the two-sample Kolmogorov-Smirnov tests. The data were found to be normally distributed, satisfying this assumption where needed for parametric testing. Mean±SEM was calculated for variables in each experimental group, then analyzed by ANOVA and Student's t-test (two-tailed) or Fisher's exact test, as appropriate. A p-value of <0.05 was considered significant.

Example 11

Expression and Characterization of Recombinant Muc3 CRD Proteins

The structures of the mucin CRD proteins used in this study are indicated in FIGS. 4 and 5. In previous studies, GST-tagged recombinant mouse Muc3 cysteine-rich domain protein (GST-Muc3-CRD1-L-CRD2) has demonstrated anti-apoptotic and pro-migratory activity in colonic cell lines. In order to determine if replacement of the large GST purification tag with a smaller $His_8$-tag altered the biologic activity of the CRD recombinant proteins, full-length His-tagged Muc3-CRD1-L-CRD2 (FIG. 5A (1)) was expressed in E. coli. This protein was shown to have an ability to stimulate cell migration in a colon epithelial cell line similar to GST-Muc3-CRD1-L-CRD2 (FIG. 6A).

Next, in order to determine the effect of the spacing between the CRD domains (CDR1 and CRD2) on biologic activity of the Muc3-CRD1-L-CRD2 protein, two recombinant proteins were made with a truncated Linker-SEA (L) domain lacking most of the SEA module, including the cleavage site, but in which the last 56 residues in the Linker-SEA region were retained; this region is defined as the L-Cys domain. In these two proteins the L-Cys domains were preceded by 11 (FIG. 5A (2)) or 20 (FIG. 5A (3)) amino acid regions designed to be of random structure. These recombinant proteins with truncated linker regions lacking most of the SEA module demonstrated no anti-apoptotic activity in a colonic cell line (FIG. 6B). In addition, a recombinant linker (L) domain protein containing the SEA module sequence and lacking the L-Cys domain and the CRD domains (FIG. 5A (4)) had no anti-apoptotic activity (FIG. 6B). Individual mouse Muc3 GST-tagged CRD1 and CRD2 proteins alone or in combination did not demonstrate anti-apoptosis cell migration properties. The data indicate that (1) smaller $His_8$-tagged recombinant CRD proteins retain biological activity compared to the previously described GST-tagged protein, and (2) anti-apoptotic activity requires a "full-length" Muc3 CRD1-L-CRD2 molecule with an intact SEA module. Proteins with truncated L domains lacking the SEA module, but containing L-Cys; proteins containing the SEA module alone, lacking CRD domains and L-Cys; and proteins with only individual CRD domains (shown previously) appear to be inactive.

Example 12

Expression and Characterization of Recombinant MUC17 CRD Proteins

In order to determine if the human homolog of the mouse Muc3 CRD protein was biologically active, a variety of GST- and His-tagged MUC17-CRD1-L-CRD2 proteins were generated in both E. coli and baculovirus-insect cell systems (FIG. 5B (5-7)). As shown in FIG. 7A, incubation of LoVo colonic cells with 10 µg/mL of each of these proteins significantly inhibited apoptosis induced by anti-Fas, which was equivalent to inhibition induced by 10 ng/mL EGF. Treatment of colon cells with increasing doses of His-tagged MUC17-CRD1-L-CRD2 demonstrated a dose response with increased levels of inhibition of apoptosis with increased doses of the recombinant protein (FIG. 7B). Both E. coli- and baculovirus-derived His-tagged-MUC17-CRD1-L-CRD2 protein induced cell migration in LoVo cells to an equivalent degree when compared with 10 ng/mL EGF (FIG. 8A). In order to test whether this response occurred in other intestinal cell lines, migration in IEC-6 intestinal cells was tested, and again a similar stimulation of cell migration by proteins derived from E. coli and insect cells was found (FIG. 8B).

Proliferation of His-tagged Muc3 and MUC17 CRD1-L-CRD2 was compared over 48 hr in the index LoVo colon cell line, using a protein concentration that was shown to maximally stimulate cell migration and inhibit apoptosis. As indicated in FIG. 9, neither of these proteins stimulated cell growth over 48 hr in comparison to cells grown in serum-free medium, in contrast to a significant increase in cell growth induced by 1% FBS. Previous studies have shown GST-tagged Muc3CRD1-L-CRD2 does not stimulate cell proliferation.

Example 13

N-Terminal Sequencing of Purified MUC17 CRD1-L-CRD2

Membrane-bound mucins contain a SEA (sea urchin sperm protein, enterokinase and agrin) module that contains a proteolytic cleavage site and sequences that are responsible for noncovalent association of protein subunits. In order to determine if the proteolytic cleavage site RLG/SVVVE within the SEA sequence in recombinant MUC17CRD1-L-CRD2 is in fact cleaved, this protein was made using the baculovirus-insect cell system and tested by sequencing the subunits separated on SDS-PAGE. As indicated in FIG. 10, N-terminal sequence analysis of baculovirus-insect cell-derived his-tagged MUC17 CRD1-L-CRD2 was performed. This recombinant protein consists of two bands at 35 and 30 kD when resolved on a reducing SDS-PAGE gel. A portion of each band was excised and the eluted protein analyzed separately, and the results are indicated in Table 1.

TABLE 1

Amino acid composition of MUC17 CRD1-L-CRD2 from Edman degradation analysis

| Cycle | 1 | 2 | 3 | 4 | 5 |
|---|---|---|---|---|---|
| Upper band [FIG. 10] | Ser (102) | Val (167) | Val (192)$^a$ | Val (167) | Glu (119) |
|  | Ala (34) | Met (30) | Val (192)$^a$ | His (12)$^a$ | His (16)$^a$ |
| Lower Band [FIG. 10] | Gly (24) | Arg (9) | Thr (31) | Thr (80)$^a$ | Thr (91)$^a$ |
|  | Met (120) | Gly (63) | Arg (30) | Thr (80)$^a$ | Thr (91)$^a$ |
|  | Ser (9) | Val (15) | Val (14)$^a$ | Val (14)$^a$ | Glu (9) |

PTH amino acids and yields (picomol) at each cycle of Edman degradation; ( ) = picomol;
$^a$ Repetitive appearances of Val, Thr, and His in individual peptides and in mixtures lead to increasing apparent yields during the analysis, while yields would be expected to diminish as one proceeds to the next cycle. Table 1 indicates one major C-terminal polypeptide, the major component of the upper band, and 3 others coming from the N-terminus the sum of which is equivalent to the C-terminal protein.

N-terminal amino acid sequence analysis demonstrated that the upper band consists of a major component beginning at the SEA cleavage site (SVVVE . . . ) with 3 glycosylation sites and a minor component beginning at the N-terminus of this construct (AMVHH . . . ), which relates to the secretion sequence used for expression, the vector His tag. There was little, if any, full-length MUC17 protein present; processing at the SEA sequence was nearly 100%. The lower band had 3 proteins, 2 of which were from the actual N-terminus of MUC17 with or without Met, probably due to proteolytic release of N-terminal Met (GRTT . . . and MGRTT . . . ). A minor component was also present starting at the SEA site with probable early C-terminal truncation to account for its smaller size. N-terminal sequencing was performed of protein eluted from a gel of recombinant MUC17-CRD1-L-CRD2 produced in E. coli, and similar evidence of cleavage at the SEA site was observed in a minor component (data not shown). These data indicate that the MUC17 recombinant protein is cleaved, as expected, at the SEA cleavage site, and the components co-purify with the final His-tagged protein.

Example 14

Cell Migration and Apoptosis

Cell migration and apoptosis are critical for normal intestinal homeostasis and for mucosal healing in response to injury. The normal intestinal barrier is maintained by the continuous migration of cells from the proliferative compartment in the lower crypts to the intestinal villi or colon surface. Following intestinal injury the ability of cells to migrate and close a wound allows for restitution of the epithelial barrier more rapidly than by enhanced proliferation. Increased cell migration occurs in response to experimental intestinal injury and peptic ulcer disease, and inflammatory diseases of the bowel. Increased cell migration and anti-apoptosis are often associated and share some common pathways. Thus, agents that enhance intestinal cell migration and reduce apoptosis are potentially therapeutic for conditions of epithelial injury.

The recombinant mouse GST-Muc3 cysteine-rich domain (CRD) protein with two cysteine-rich EGF-like domains has been shown to be able to inhibit apoptosis and stimulate cell migration in colonic epithelial cells, and was able to enhance healing of experimental mouse models of colitis. As described herein, the activity of the mucin cysteine-rich domain proteins was shown to require a full-length linker segment between the two CRD units, including the full SEA module, and that a smaller sized recombinant protein can be effectively achieved by substituting a His$_8$-tag for the GST purification tag. The experiments described in the Examples herein have also been extended to include the demonstration that the human ortholog of the mouse Muc3 cysteine-rich protein, MUC17 CRD1-L-CRD2, has similar biologic activity in vitro, regardless of whether the protein is synthesized in E. coli or in insect cells. Baculovirus-infected insect cells were chosen as an exemplary eukaryotic system that would afford properly folded material for production of MUC17 CRD1-L-CRD2 polypeptide. These experimental results in the Examples above provide evidence that MUC17 CRD1-L-CRD2 polypeptide refolded from bacterial inclusion bodies is equivalent to properly folded protein made in a eukaryotic host. In addition, it should be noted that glycosylation of proteins can occur when synthesized in eukaryotic cells, whereas proteins made in bacteria do not undergo glycosylation. Given the fact that the molecular weights of fragments observed upon analysis of the MUC17-CRD1-L-CRD2 polypeptide produced in insect cells were considerably higher than expected on the basis of amino acid composition (FIG. 10), this protein was most likely glycosylated at its various N-glycosylation sites. Testing of MUC17-CRD1-L-CRD2 polypeptides derived from bacteria and insect cells indicated that the function did not appear altered despite the fact that the insect cell protein was N-glycosylated.

Although the present Examples did not use mammalian cells for protein synthesis, it is believed that the use of mammalian cells would have resulted in proteins with the most "native" glycosylation pattern. MUC17 CRD1-L-CRD2 polypeptide produced from insect cells affords the advantage in quickly providing recombinant proteins that are properly folded and active in amounts needed for biological studies. Future experiments would include developing a transformed mammalian cell line, such as CHO, which is a generally accepted host for making protein therapeutics that are both properly folded and glycosylated.

The oxidation state of Cys residues in CRD1-L-CRD2 has not been determined. The Cys-rich region of mucins can be divided into various regions with respect to the EGF-like CRD units. This is done in FIG. 1B, where it can be seen that CRD1 and CRD2 have an arrangement of Cys 422 residues suggestive of a relationship with EGF. This accounts for 12 Cys residues in CRD1; but there are additional Cys residues in the entire recombinant protein. Not to be limited by theory, the existence of 4 highly conserved Cys residues in the region of the Linker region just preceding CRD2 (FIG. 4C) suggests that these residues are also paired in one or more disulfide linkages. These residues serve to define a Cys-containing structural element in the linker region that is herein defined as the L-Cys domain. Not to be limited by theory, L-Cys may be separate from the CRD units, and may have some other function in the mucin molecule. Our studies have not delineated a function for L-Cys. Thus far, 16 Cys residues in this recombinant protein that are best referred to as potential disulfide-bonded Cys residues have been considered. Further delineation of the role of individual Cys residues in these recombinant proteins may be accomplished by site-directed mutagenesis studies. In addition, a comparison of the segment preceding CRD1 is indicated in FIG. 4D. Note that Cys residues are seen in MUC3 and Muc3, but not MUC17; however, whether this results in differences in structure or aggregation of these proteins has not been determined.

Within the Linker-SEA region is the SEA module, which is highly conserved among membrane-bound mucins and contains an autocatalytic cleavage site and amino acid sequences required for the noncovalent association of cleaved subunits. Others have previously shown that a recombinant MUC1 mucin SEA protein produced in *E. coli* undergoes autocatalytic cleavage at the GSSV sequence, indicating that the SEA cleavage process may occur in proteins produced in *E. coli* as well as eukaryotic cells. The results presented in the Examples herein have demonstrated that the purified His-tagged MUC17CRD1-L-CRD2 recombinant protein contains mixtures of proteins with evidence of cleavage at the predicted SEA cleavage site.

This cleavage may be important for the functioning of the linker region of the recombinant protein, since smaller linker regions without the SEA module have no activity. It has been previously shown that individual mouse Muc3 GST tagged CRD1 and CRD2 proteins alone or in combination were not biologically active. In addition, the recombinant Muc3 proteins in (FIG. 5A (2 & 3)) included a modified Linker-SEA domain in which a portion of the SEA domain was removed, including the SEA cleavage site, which resulted in a loss of biological activity. This strongly suggests that the presence of the SEA module is required for the observed activity of the recombinant protein. The protein in (FIG. 5A (4)) contained only the SEA module, without the remainder of the Linker region or the CRD domains, and this protein also demonstrated no biological activity. These data suggest that the full-length CRD1-L-CRD2 polypeptide with an intact SEA domain is required for the protein to be fully functional. Others have shown that within the SEA module several N-glycosylation sites flanking the GSVVV cleavage site may control the extent of cleavage that occurs at this cleavage site, indicating the functional importance of the full SEA module.

The present experiments detailed in the Examples given herein have provided insight into the mechanisms whereby membrane-bound mucins and their cysteine-rich domains (CRD) influence cell migration and anti-apoptosis. The morphologic assay used to measure apoptosis was a rapid overall assay of total apoptosis, and does not distinguish between early and late apoptosis. Also, the specific mechanism for inhibition of apoptosis was not determined, and may involve induction of anti-apoptotic proteins via a PI3-kinase pathway or by targeting the caspase-9 enzyme, as has been shown for trefoil factor (TFF) proteins. It has been previously demonstrated that the recombinant mouse GST-Muc3 cysteine-rich domain (CRD) protein did not stimulate erbB or EGF-type receptors. However, it is noted that EGF-type receptors remain likely candidate interacting proteins, and further experiments using more sensitive techniques to determine whether mucin CRD proteins cause clustering or internalization of erbB receptors are required.

In conclusion, these Examples have provided evidentiary support that full-length human MUC17 mucin-derived CRD polypeptides produced in *E. coli* or in a eukaryotic expression system are feasible and promising candidates as a therapeutic for conditions associated with epithelial cell injury, such as inflammatory bowel disease (IBD), mucositis, other colitides and related gastrointestinal diseases and disorders.

While the present technology has been illustrated and exemplified throughout the description and in the Examples, it is obvious to one of ordinary skill that many changes may be made in the details of the process of assembly without departing from the spirit and scope of this disclosure.

What is claimed is:

1. A purified mucin 17 (MUC17) derived polypeptide, the polypeptide consisting of the amino acid sequence selected from SEQ ID NO: 4, and SEQ ID NO: 5, wherein the polypeptide is conjugated to one or more of a plural His tag, a FLAG-tag or a GST-tag, or a therapeutically acceptable salt thereof.

2. A pharmaceutical composition comprising a therapeutically effective amount of a MUC17 derived polypeptide of claim 1 and a pharmaceutical excipient, wherein the pharmaceutical composition is formulated for oral, parental, or rectal administration in a solid, liquid or aerosol form.

3. The pharmaceutical composition of claim 2, wherein the pharmaceutical composition further comprises a second active agent.

4. The pharmaceutical composition of claim 3, wherein the second agent is selected from the group consisting of: aminosalicylates, acetaminophen, laxatives, non-steroidal anti-inflammatory drug substances (NSAIDS), antibiotics, corticosteroids, anti-diarrheals and immune modifying agents.

5. A method for treating a gastrointestinal disease or disorder in a subject in need thereof, the method comprising: administering a therapeutically effective amount of a MUC17 derived polypeptide of claim 1, wherein the gastrointestinal disease or disorder is selected from irritable bowel syndrome, ulcerative colitis, mucositis, Crohn's disease, chronic colitis, microscopic colitis, indeterminate colitis, ileal inflammation and diverticulitis.

6. The method of claim 5, wherein administering the therapeutically effective amount of MUC17 derived polypeptide comprises administering the MUC17 derived polypeptide orally, parentally, rectally or combinations thereof.

7. The method of claim 6, wherein the therapeutically effective amount of MUC17 derived polypeptide is administered orally or rectally.

8. The method of claim 5, wherein the therapeutically effective amount of the MUC17, derived polypeptide administered to a subject is administered in an amount ranging from about 0.01 to about 100 mg/kg body weight/day.

9. The method of claim 5, wherein the therapeutically effective amount of the MUC17, derived polypeptide administered to a subject is administered in an amount ranging from about 0.5 to about 5 mg/kg body weight/day.

* * * * *

SEQUENCE LISTING

```
<160> NUMBER OF SEQ ID NOS: 12

<210> SEQ ID NO 1
<211> LENGTH: 258
<212> TYPE: PRT
<213> ORGANISM: Homo sapiens
<220> FEATURE:
<221> NAME/KEY: MISC_FEATURE
<222> LOCATION: (1)..(258)
<223> OTHER INFORMATION: (MUC17 CRD1-L-CRD2 polypeptide)

<400> SEQUENCE: 1

Arg Thr Thr Thr Cys Phe Gly Asp Gly Cys Gln Asn Thr Ala Ser Arg
1               5                   10                  15

Cys Lys Asn Gly Gly Thr Trp Asp Gly Leu Lys Cys Gln Cys Pro Asn
            20                  25                  30
```

Leu Tyr Tyr Gly Glu Leu Cys Glu Glu Val Val Ser Ser Ile Asp Ile
                35                  40                  45

Gly Pro Pro Glu Thr Ile Ser Ala Gln Met Glu Leu Thr Val Thr Val
    50                  55                  60

Thr Ser Val Lys Phe Thr Glu Glu Leu Lys Asn His Ser Ser Gln Glu
65                  70                  75                  80

Phe Gln Glu Phe Lys Gln Thr Phe Thr Glu Gln Met Asn Ile Val Tyr
                85                  90                  95

Ser Gly Ile Pro Glu Tyr Val Gly Val Asn Ile Thr Lys Leu Arg Leu
            100                 105                 110

Gly Ser Val Val Val Glu His Asp Val Leu Leu Arg Thr Lys Tyr Thr
            115                 120                 125

Pro Glu Tyr Lys Thr Val Leu Asp Asn Ala Thr Glu Val Val Lys Glu
            130                 135                 140

Lys Ile Thr Lys Val Thr Thr Gln Gln Ile Met Ile Asn Asp Ile Cys
145                 150                 155                 160

Ser Asp Met Met Cys Phe Asn Thr Thr Gly Thr Gln Val Gln Asn Ile
                165                 170                 175

Thr Val Thr Gln Tyr Asp Pro Glu Glu Asp Cys Arg Lys Met Ala Lys
            180                 185                 190

Glu Tyr Gly Asp Tyr Phe Val Val Glu Tyr Arg Asp Gln Lys Pro Tyr
            195                 200                 205

Cys Ile Ser Pro Cys Glu Pro Gly Phe Ser Val Ser Lys Asn Cys Asn
            210                 215                 220

Leu Gly Lys Cys Gln Met Ser Leu Ser Gly Pro Gln Cys Leu Cys Val
225                 230                 235                 240

Thr Thr Glu Thr His Trp Tyr Ser Gly Glu Cys Asn Gln Gly Thr
                245                 250                 255

Gln Lys

<210> SEQ ID NO 2
<211> LENGTH: 259
<212> TYPE: PRT
<213> ORGANISM: Homo sapiens
<220> FEATURE:
<221> NAME/KEY: MISC_FEATURE
<222> LOCATION: (1)..(259)
<223> OTHER INFORMATION: (MUC17 CRD1-L-CRD2 polypeptide) (Serine
      C-terminal A.A.)

<400> SEQUENCE: 2

Arg Thr Thr Thr Cys Phe Gly Asp Gly Cys Gln Asn Thr Ala Ser Arg
1               5                   10                  15

Cys Lys Asn Gly Gly Thr Trp Asp Gly Leu Lys Cys Gln Cys Pro Asn
                20                  25                  30

Leu Tyr Tyr Gly Glu Leu Cys Glu Glu Val Val Ser Ser Ile Asp Ile
                35                  40                  45

Gly Pro Pro Glu Thr Ile Ser Ala Gln Met Glu Leu Thr Val Thr Val
    50                  55                  60

Thr Ser Val Lys Phe Thr Glu Glu Leu Lys Asn His Ser Ser Gln Glu
65                  70                  75                  80

Phe Gln Glu Phe Lys Gln Thr Phe Thr Glu Gln Met Asn Ile Val Tyr
                85                  90                  95

Ser Gly Ile Pro Glu Tyr Val Gly Val Asn Ile Thr Lys Leu Arg Leu
            100                 105                 110

Gly Ser Val Val Val Glu His Asp Val Leu Leu Arg Thr Lys Tyr Thr

```
                115                 120                 125
Pro Glu Tyr Lys Thr Val Leu Asp Asn Ala Thr Glu Val Val Lys Glu
    130                 135                 140

Lys Ile Thr Lys Val Thr Thr Gln Gln Ile Met Ile Asn Asp Ile Cys
145                 150                 155                 160

Ser Asp Met Met Cys Phe Asn Thr Thr Gly Thr Gln Val Gln Asn Ile
                165                 170                 175

Thr Val Thr Gln Tyr Asp Pro Glu Glu Asp Cys Arg Lys Met Ala Lys
            180                 185                 190

Glu Tyr Gly Asp Tyr Phe Val Val Glu Tyr Arg Asp Gln Lys Pro Tyr
        195                 200                 205

Cys Ile Ser Pro Cys Glu Pro Gly Phe Ser Val Ser Lys Asn Cys Asn
    210                 215                 220

Leu Gly Lys Cys Gln Met Ser Leu Ser Gly Pro Gln Cys Leu Cys Val
225                 230                 235                 240

Thr Thr Glu Thr His Trp Tyr Ser Gly Glu Thr Cys Asn Gln Gly Thr
                245                 250                 255

Gln Lys Ser

<210> SEQ ID NO 3
<211> LENGTH: 207
<212> TYPE: PRT
<213> ORGANISM: Homo sapiens
<220> FEATURE:
<221> NAME/KEY: MISC_FEATURE
<222> LOCATION: (1)..(207)
<223> OTHER INFORMATION: (MUC17 CRD1-L polypeptide)

<400> SEQUENCE: 3

Arg Thr Thr Thr Cys Phe Gly Asp Gly Cys Gln Asn Thr Ala Ser Arg
1               5                   10                  15

Cys Lys Asn Gly Gly Thr Trp Asp Gly Leu Lys Cys Gln Cys Pro Asn
            20                  25                  30

Leu Tyr Tyr Gly Glu Leu Cys Glu Glu Val Val Ser Ser Ile Asp Ile
        35                  40                  45

Gly Pro Pro Glu Thr Ile Ser Ala Gln Met Glu Leu Thr Val Thr Val
    50                  55                  60

Thr Ser Val Lys Phe Thr Glu Glu Leu Lys Asn His Ser Ser Gln Glu
65                  70                  75                  80

Phe Gln Glu Phe Lys Gln Thr Phe Thr Glu Gln Met Asn Ile Val Tyr
                85                  90                  95

Ser Gly Ile Pro Glu Tyr Val Gly Val Asn Ile Thr Lys Leu Arg Leu
            100                 105                 110

Gly Ser Val Val Val Glu His Asp Val Leu Leu Arg Thr Lys Tyr Thr
        115                 120                 125

Pro Glu Tyr Lys Thr Val Leu Asp Asn Ala Thr Glu Val Val Lys Glu
    130                 135                 140

Lys Ile Thr Lys Val Thr Thr Gln Gln Ile Met Ile Asn Asp Ile Cys
145                 150                 155                 160

Ser Asp Met Met Cys Phe Asn Thr Thr Gly Thr Gln Val Gln Asn Ile
                165                 170                 175

Thr Val Thr Gln Tyr Asp Pro Glu Glu Asp Cys Arg Lys Met Ala Lys
            180                 185                 190

Glu Tyr Gly Asp Tyr Phe Val Val Glu Tyr Arg Asp Gln Lys Pro
        195                 200                 205
```

<210> SEQ ID NO 4
<211> LENGTH: 206
<212> TYPE: PRT
<213> ORGANISM: Homo sapiens
<220> FEATURE:
<221> NAME/KEY: MISC_FEATURE
<222> LOCATION: (1)..(206)
<223> OTHER INFORMATION: (MUC17 L-CRD2 polypeptide)

<400> SEQUENCE: 4

Thr Ile Ser Ala Gln Met Glu Leu Thr Val Thr Val Thr Ser Val Lys
1               5                   10                  15

Phe Thr Glu Glu Leu Lys Asn His Ser Ser Gln Glu Phe Gln Glu Phe
            20                  25                  30

Lys Gln Thr Phe Thr Glu Gln Met Asn Ile Val Tyr Ser Gly Ile Pro
        35                  40                  45

Glu Tyr Val Gly Val Asn Ile Thr Lys Leu Arg Leu Gly Ser Val Val
    50                  55                  60

Val Glu His Asp Val Leu Leu Arg Thr Lys Tyr Thr Pro Glu Tyr Lys
65                  70                  75                  80

Thr Val Leu Asp Asn Ala Thr Glu Val Val Lys Glu Lys Ile Thr Lys
                85                  90                  95

Val Thr Thr Gln Gln Ile Met Ile Asn Asp Ile Cys Ser Asp Met Met
            100                 105                 110

Cys Phe Asn Thr Thr Gly Thr Gln Val Gln Asn Ile Thr Val Thr Gln
        115                 120                 125

Tyr Asp Pro Glu Glu Asp Cys Arg Lys Met Ala Lys Glu Tyr Gly Asp
    130                 135                 140

Tyr Phe Val Val Glu Tyr Arg Asp Gln Lys Pro Tyr Cys Ile Ser Pro
145                 150                 155                 160

Cys Glu Pro Gly Phe Ser Val Ser Lys Asn Cys Asn Leu Gly Lys Cys
                165                 170                 175

Gln Met Ser Leu Ser Gly Pro Gln Cys Leu Cys Val Thr Thr Glu Thr
            180                 185                 190

His Trp Tyr Ser Gly Glu Thr Cys Asn Gln Gly Thr Gln Lys
        195                 200                 205

<210> SEQ ID NO 5
<211> LENGTH: 207
<212> TYPE: PRT
<213> ORGANISM: Homo sapiens
<220> FEATURE:
<221> NAME/KEY: MISC_FEATURE
<222> LOCATION: (1)..(207)
<223> OTHER INFORMATION: (MUC17 L-CRD2 polypeptide) (Serine C-terminal
      A.A.)

<400> SEQUENCE: 5

Thr Ile Ser Ala Gln Met Glu Leu Thr Val Thr Val Thr Ser Val Lys
1               5                   10                  15

Phe Thr Glu Glu Leu Lys Asn His Ser Ser Gln Glu Phe Gln Glu Phe
            20                  25                  30

Lys Gln Thr Phe Thr Glu Gln Met Asn Ile Val Tyr Ser Gly Ile Pro
        35                  40                  45

Glu Tyr Val Gly Val Asn Ile Thr Lys Leu Arg Leu Gly Ser Val Val
    50                  55                  60

Val Glu His Asp Val Leu Leu Arg Thr Lys Tyr Thr Pro Glu Tyr Lys
65                  70                  75                  80

```
Thr Val Leu Asp Asn Ala Thr Glu Val Val Lys Glu Lys Ile Thr Lys
                85                  90                  95

Val Thr Thr Gln Gln Ile Met Ile Asn Asp Ile Cys Ser Asp Met Met
            100                 105                 110

Cys Phe Asn Thr Thr Gly Thr Gln Val Gln Asn Ile Thr Val Thr Gln
            115                 120                 125

Tyr Asp Pro Glu Glu Asp Cys Arg Lys Met Ala Lys Glu Tyr Gly Asp
            130                 135                 140

Tyr Phe Val Val Glu Tyr Arg Asp Gln Lys Pro Tyr Cys Ile Ser Pro
145                 150                 155                 160

Cys Glu Pro Gly Phe Ser Val Ser Lys Asn Cys Asn Leu Gly Lys Cys
                165                 170                 175

Gln Met Ser Leu Ser Gly Pro Gln Cys Leu Cys Val Thr Thr Glu Thr
                180                 185                 190

His Trp Tyr Ser Gly Glu Thr Cys Asn Gln Gly Thr Gln Lys Ser
                195                 200                 205

<210> SEQ ID NO 6
<211> LENGTH: 286
<212> TYPE: PRT
<213> ORGANISM: Mus musculus
<220> FEATURE:
<221> NAME/KEY: MISC_FEATURE
<222> LOCATION: (1)..(286)
<223> OTHER INFORMATION: Mouse Muc3 CRD1-L-CRD2-Hst8 (I-1 through G-266)
<220> FEATURE:
<221> NAME/KEY: MISC_FEATURE
<222> LOCATION: (13)..(13)
<223> OTHER INFORMATION: I-1
<220> FEATURE:
<221> NAME/KEY: MISC_FEATURE
<222> LOCATION: (278)..(278)
<223> OTHER INFORMATION: G-266

<400> SEQUENCE: 6

Cys Met Asn Gly Gly Phe Trp Thr Gly Asp Lys Cys Ile Cys Pro Asn
1               5                   10                  15

Gly Phe Gly Gly Asp Arg Cys Glu Asn Ile Val Asn Val Asn Cys
                20                  25                  30

Glu Asn Gly Gly Thr Trp Asp Gly Leu Lys Cys Gln Cys Thr Ser Leu
            35                  40                  45

Phe Tyr Gly Pro Arg Cys Glu Glu Leu Val Glu Ser Val Glu Ile Glu
50                  55                  60

Pro Thr Val Ala Ala Ser Val Glu Val Ser Val Thr Val Thr Ser Gln
65                  70                  75                  80

Glu Tyr Ser Glu Lys Leu Gln Asp Arg Lys Ser Glu Glu Phe Ser Asn
                85                  90                  95

Phe Asn Lys Thr Phe Thr Lys Gln Met Ala Leu Ile Tyr Ala Gly Ile
            100                 105                 110

Pro Glu Tyr Glu Gly Val Ile Ile Lys Asn Leu Ser Lys Gly Ser Ile
            115                 120                 125

Val Val Asp Tyr Asp Val Ile Leu Lys Ala Lys Tyr Thr Pro Gly Phe
130                 135                 140

Glu Asn Thr Leu Asp Thr Val Val Lys Asn Leu Glu Thr Lys Ile Lys
145                 150                 155                 160

Asn Ala Thr Glu Val Gln Val Gln Asp Val Asn Asn Cys Ser Ala
            165                 170                 175

Leu Leu Cys Phe Asn Ser Thr Ala Thr Lys Val Gln Asn Ser Ala Thr
            180                 185                 190
```

```
Val Ser Val Asn Pro Glu Glu Thr Cys Lys Lys Glu Ala Gly Glu Asp
        195                 200                 205

Phe Ala Lys Phe Val Thr Leu Gly Gln Lys Gly Asp Lys Trp Phe Cys
        210                 215                 220

Ile Thr Pro Cys Ser Ala Gly Tyr Ser Thr Ser Lys Asn Cys Ser Tyr
225                 230                 235                 240

Gly Lys Cys Gln Leu Gln Arg Ser Gly Pro Gln Cys Leu Cys Leu Ile
                245                 250                 255

Thr Asp Thr His Trp Tyr Ser Gly Glu Asn Cys Asp Trp Gly Ile Gln
                260                 265                 270

Lys Ser Leu Val Tyr Gly His His His His His His His
        275                 280                 285
```

<210> SEQ ID NO 7
<211> LENGTH: 186
<212> TYPE: PRT
<213> ORGANISM: Mus musculus
<220> FEATURE:
<221> NAME/KEY: MISC_FEATURE
<222> LOCATION: (1)..(186)
<223> OTHER INFORMATION: Mouse Muc-3 CRD1-(11 amino acid spacer) L-Cys
    domain - CRD2

<400> SEQUENCE: 7

```
Cys Met Asn Gly Gly Phe Trp Thr Gly Asp Lys Cys Ile Cys Pro Asn
1               5                   10                  15

Gly Phe Gly Gly Asp Arg Cys Glu Asn Ile Val Asn Val Val Asn Cys
                20                  25                  30

Glu Asn Gly Gly Thr Trp Asp Gly Leu Lys Cys Gln Cys Thr Ser Leu
                35                  40                  45

Phe Tyr Gly Pro Arg Cys Glu Glu Leu Val Glu Pro Gly Ser Gly Ser
        50                  55                  60

Asp Gly Ser Asp Gly Ser Asn Asn Cys Ser Ala Leu Leu Cys Phe
65                  70                  75                  80

Asn Ser Thr Ala Thr Lys Val Gln Asn Ser Ala Thr Val Ser Val Asn
                85                  90                  95

Pro Glu Glu Thr Cys Lys Lys Glu Ala Gly Glu Asp Phe Ala Lys Phe
                100                 105                 110

Val Thr Leu Gly Gln Lys Gly Asp Lys Trp Phe Cys Ile Thr Pro Cys
                115                 120                 125

Ser Ala Gly Tyr Ser Thr Ser Lys Asn Cys Ser Tyr Gly Lys Cys Gln
                130                 135                 140

Leu Gln Arg Ser Gly Pro Gln Cys Leu Cys Leu Ile Thr Asp Thr His
145                 150                 155                 160

Trp Tyr Ser Gly Glu Asn Cys Asp Trp Gly Ile Gln Lys Ser Ile Val
                165                 170                 175

Tyr Gly His His His His His His His
                180                 185
```

<210> SEQ ID NO 8
<211> LENGTH: 195
<212> TYPE: PRT
<213> ORGANISM: Mus musculus
<220> FEATURE:
<221> NAME/KEY: MISC_FEATURE
<222> LOCATION: (1)..(195)
<223> OTHER INFORMATION: Mouse Muc-3 CRD1-(20 amino acid spacer) L-Cys
    domain - CRD2
<220> FEATURE:

```
<221> NAME/KEY: MISC_FEATURE
<222> LOCATION: (1)..(195)
<223> OTHER INFORMATION: Mouse Muc-3 CRD1-(20 amino acid spacer)
      L-Cys - CRD2

<400> SEQUENCE: 8
```

Cys Met Asn Gly Gly Phe Trp Thr Gly Asp Lys Cys Ile Cys Pro Asn
1               5                   10                  15

Gly Phe Gly Gly Asp Arg Cys Glu Asn Ile Val Asn Val Val Asn Cys
            20                  25                  30

Glu Asn Gly Gly Thr Trp Asp Gly Leu Lys Cys Gln Cys Thr Ser Leu
        35                  40                  45

Phe Tyr Gly Pro Arg Cys Glu Glu Leu Val Glu Phe Leu Lys Pro Gln
    50                  55                  60

His Pro Gly Ser Gly Ser Asp Gly Ser Asp Gly Ser Ala Gln Ile Asn
65              70                  75                  80

Asn Asn Cys Ser Ala Leu Leu Cys Phe Asn Ser Thr Ala Thr Lys Val
                85                  90                  95

Gln Asn Ser Ala Thr Val Ser Val Asn Pro Glu Thr Cys Lys Lys
            100                 105                 110

Glu Ala Gly Glu Asp Phe Ala Lys Phe Val Thr Leu Gly Gln Lys Gly
            115                 120                 125

Asp Lys Trp Phe Cys Ile Thr Pro Cys Ser Ala Gly Tyr Ser Thr Ser
130                 135                 140

Lys Asn Cys Ser Tyr Gly Lys Cys Gln Leu Gln Arg Ser Gly Pro Gln
145                 150                 155                 160

Cys Leu Cys Leu Ile Thr Asp Thr His Trp Tyr Ser Gly Glu Asn Cys
                165                 170                 175

Asp Trp Gly Ile Gln Lys Ser Ile Val Tyr Gly His His His His
            180                 185                 190

His His His
        195

```
<210> SEQ ID NO 9
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Linker domain-SEA module Muc 3

<400> SEQUENCE: 9
```

Ser Val Glu Ile Glu Pro Thr Val Ala Ala Ser Val Glu Val Ser Val
1               5                   10                  15

Thr Val Thr Ser Gln Glu Tyr Ser Glu Lys Leu Gln Asp Arg Lys Ser
            20                  25                  30

Glu Glu Phe Ser Asn Phe Asn Lys Thr Phe Thr Lys Gln Met Ala Leu
        35                  40                  45

Ile Tyr Ala Gly Ile Pro Glu Tyr Gly Val Ile Ile Lys Asn Leu
    50                  55                  60

Ser Lys Gly Ser Ile Val Val Asp Tyr Asp Val Ile Leu Lys Ala Lys
65              70                  75                  80

Tyr Thr Pro Gly Phe Glu Asn Thr Leu Asp Thr Val Val Lys Asn Leu
                85                  90                  95

Glu Thr Lys Ile Lys Asn Ala Thr Glu Val Gln Val Gln Asp Val
            100                 105                 110

```
<210> SEQ ID NO 10
<211> LENGTH: 259
<212> TYPE: PRT
<213> ORGANISM: Homo sapiens
<220> FEATURE:
<221> NAME/KEY: MISC_FEATURE
<222> LOCATION: (1)..(259)
<223> OTHER INFORMATION: Human GST-MUC17CRD1-Linker-CRD2 (R-1 through
    S-260)
<220> FEATURE:
<221> NAME/KEY: MISC_FEATURE
<222> LOCATION: (1)..(1)
<223> OTHER INFORMATION: linked to (Glutathione-S-Transferase)

<400> SEQUENCE: 10
```

Arg Thr Thr Thr Cys Phe Gly Asp Gly Cys Gln Asn Thr Ala Ser Arg
1               5                   10                  15

Cys Lys Asn Gly Gly Thr Trp Asp Gly Leu Lys Cys Gln Cys Pro Asn
            20                  25                  30

Leu Tyr Tyr Gly Glu Leu Cys Glu Val Val Ser Ser Ile Asp Ile
        35                  40                  45

Gly Pro Pro Glu Thr Ile Ser Ala Gln Met Glu Leu Thr Val Thr Val
    50                  55                  60

Thr Ser Val Lys Phe Thr Glu Glu Leu Lys Asn His Ser Ser Gln Glu
65                  70                  75                  80

Phe Gln Glu Phe Lys Gln Thr Phe Thr Glu Gln Met Asn Ile Val Tyr
                85                  90                  95

Ser Gly Ile Pro Glu Tyr Val Gly Val Asn Ile Thr Lys Leu Arg Leu
            100                 105                 110

Gly Ser Val Val Val Glu His Asp Val Leu Leu Arg Thr Lys Tyr Thr
        115                 120                 125

Pro Glu Tyr Lys Thr Val Leu Asp Asn Ala Thr Glu Val Val Lys Glu
    130                 135                 140

Lys Ile Thr Lys Val Thr Thr Gln Gln Ile Met Ile Asn Asp Ile Cys
145                 150                 155                 160

Ser Asp Met Met Cys Phe Asn Thr Thr Gly Thr Gln Val Gln Asn Ile
                165                 170                 175

Thr Val Thr Gln Tyr Asp Pro Glu Glu Asp Cys Arg Lys Met Ala Lys
            180                 185                 190

Glu Tyr Gly Asp Tyr Phe Val Val Glu Tyr Arg Asp Gln Lys Pro Tyr
        195                 200                 205

Cys Ile Ser Pro Cys Glu Pro Gly Phe Ser Val Ser Lys Asn Cys Asn
    210                 215                 220

Leu Gly Lys Cys Gln Met Ser Leu Ser Gly Pro Gln Cys Leu Cys Val
225                 230                 235                 240

Thr Thr Glu Thr His Trp Tyr Ser Gly Glu Thr Cys Asn Gln Gly Thr
                245                 250                 255

Gln Lys Ser

```
<210> SEQ ID NO 11
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)
<223> OTHER INFORMATION: Human MUC17CRD1-L-CRD2-His8 (R-1 through K-259)

<400> SEQUENCE: 11
```

Met Arg Thr Thr Thr Cys Phe Gly Asp Gly Cys Gln Asn Thr Ala Ser
1               5                   10                  15

Arg Cys Lys Asn Gly Gly Thr Trp Asp Gly Leu Lys Cys Gln Cys Pro
            20                  25                  30

Asn Leu Tyr Tyr Gly Glu Leu Cys Glu Glu Val Val Ser Ser Ile Asp
        35                  40                  45

Ile Gly Pro Pro Glu Thr Ile Ser Ala Gln Met Glu Leu Thr Val Thr
50                  55                  60

Val Thr Ser Val Lys Phe Thr Glu Glu Leu Lys Asn His Ser Ser Gln
65                  70                  75                  80

Glu Phe Gln Glu Phe Lys Gln Thr Phe Thr Glu Gln Met Asn Ile Val
                85                  90                  95

Tyr Ser Gly Ile Pro Glu Tyr Val Gly Val Asn Ile Thr Lys Leu Arg
            100                 105                 110

Leu Gly Ser Val Val Val Glu His Asp Val Leu Leu Arg Thr Lys Tyr
        115                 120                 125

Thr Pro Glu Tyr Lys Thr Val Leu Asp Asn Ala Thr Glu Val Val Lys
    130                 135                 140

Glu Lys Ile Thr Lys Val Thr Thr Gln Gln Ile Met Ile Asn Asp Ile
145                 150                 155                 160

Cys Ser Asp Met Met Cys Phe Asn Thr Thr Gly Thr Gln Val Gln Asn
                165                 170                 175

Ile Thr Val Thr Gln Tyr Asp Pro Glu Glu Asp Cys Arg Lys Met Ala
            180                 185                 190

Lys Glu Tyr Gly Asp Tyr Phe Val Val Glu Tyr Arg Asp Gln Lys Pro
        195                 200                 205

Tyr Cys Ile Ser Pro Cys Glu Pro Gly Phe Ser Val Ser Lys Asn Cys
    210                 215                 220

Asn Leu Gly Lys Cys Gln Met Ser Leu Ser Gly Pro Gln Cys Leu Cys
225                 230                 235                 240

Val Thr Thr Glu Thr His Trp Tyr Ser Gly Glu Thr Cys Asn Gln Gly
                245                 250                 255

Thr Gln Lys Ser Ile Val Tyr Gly His His His His His His His
        260                 265                 270

<210> SEQ ID NO 12
<211> LENGTH: 335
<212> TYPE: PRT
<213> ORGANISM: Homo sapiens
<220> FEATURE:
<221> NAME/KEY: MISC_FEATURE
<222> LOCATION: (1)..(335)
<223> OTHER INFORMATION: Full-length sequence of MUC17 CRD1=L-CRD2 as
      expressed in baculovirus-insect cell system

<400> SEQUENCE: 12

Ala Met Val His His His His His Ser Ala Gly Leu Val Pro Arg
1               5                   10                  15

Gly Ser Gly Lys Glu Thr Ala Ala Lys Phe Glu Arg Gln His Met
            20                  25                  30

Asp Ser Ala Ser Gly Gly Gly Asp Asp Asp Lys Ser Pro Gly Phe
        35                  40                  45

Ser Ser Lys Gly Leu Asp Pro Asn Ser Ser Lys Leu Ser Met Gly
    50                  55                  60

Arg Thr Thr Thr Cys Phe Gly Asp Gly Cys Gln Asn Thr Ala Ser Arg
65                  70                  75                  80

-continued

```
Cys Lys Asn Gly Gly Thr Trp Asp Gly Leu Lys Cys Gln Cys Pro Asn
            85              90              95

Leu Tyr Tyr Gly Glu Leu Cys Glu Glu Val Val Ser Ser Ile Asp Ile
            100             105             110

Gly Pro Pro Glu Thr Ile Ser Ala Gln Met Glu Leu Thr Val Thr Val
            115             120             125

Thr Ser Val Lys Phe Thr Glu Glu Leu Lys Asn His Ser Ser Gln Glu
    130             135             140

Phe Gln Glu Phe Lys Gln Thr Phe Thr Glu Gln Met Asn Ile Val Tyr
145             150             155             160

Ser Gly Ile Pro Glu Tyr Val Gly Val Asn Ile Thr Lys Leu Arg Leu
            165             170             175

Gly Ser Val Val Val Glu His Asp Val Leu Leu Arg Thr Lys Tyr Thr
            180             185             190

Pro Glu Tyr Lys Thr Val Leu Asp Asn Ala Thr Glu Val Val Lys Glu
            195             200             205

Lys Ile Thr Lys Val Thr Thr Gln Gln Ile Met Ile Asn Asp Ile Cys
    210             215             220

Ser Asp Met Met Cys Phe Asn Thr Thr Gly Thr Gln Val Gln Asn Ile
225             230             235             240

Thr Val Thr Gln Tyr Asp Pro Glu Glu Asp Cys Arg Lys Met Ala Lys
            245             250             255

Glu Tyr Gly Asp Tyr Phe Val Val Glu Tyr Arg Asp Gln Lys Pro Tyr
            260             265             270

Cys Ile Ser Pro Cys Glu Pro Gly Phe Ser Val Ser Lys Asn Cys Asn
    275             280             285

Leu Gly Lys Cys Gln Met Ser Leu Ser Gly Pro Gln Cys Leu Cys Val
    290             295             300

Thr Thr Glu Thr His Trp Tyr Ser Gly Glu Thr Cys Asn Gln Gly Thr
305             310             315             320

Gln Lys Ser Ile Val Tyr Gly His His His His His His His
            325             330             335
```